US012625123B2

(12) United States Patent
Diaz et al.

(10) Patent No.: US 12,625,123 B2
(45) Date of Patent: May 12, 2026

(54) DEVICE AND METHOD FOR THE ANALYTICAL AND SENSORY DETERMINATION OF THE RELEASE OF AN ACTIVE SUBSTANCE FROM A RELEASE SYSTEM

(71) Applicant: SYMRISE AG, Holzminden (DE)

(72) Inventors: Edison Diaz, Goslar (DE); Isabel Lanfermann, Goettingen (DE); Katharina Michels, Seesen (DE); Marco Singer, Holzminden (DE); Patrick Ostermann, Hoexter (DE); Achim Schumann, Northeim (DE); Fabian Ude, Einbeck (DE)

(73) Assignee: SYMRISE AG, Holzminden (DE)

( * ) Notice: Subject to any disclaimer, the term of this patent is extended or adjusted under 35 U.S.C. 154(b) by 1021 days.

(21) Appl. No.: 17/780,772

(22) PCT Filed: Nov. 27, 2019

(86) PCT No.: PCT/EP2019/082811
§ 371 (c)(1),
(2) Date: May 27, 2022

(87) PCT Pub. No.: WO2021/104624
PCT Pub. Date: Jun. 3, 2021

(65) Prior Publication Data
US 2022/0412937 A1 Dec. 29, 2022

(51) Int. Cl.
*G01N 33/15* (2006.01)
*G01N 1/02* (2006.01)
(Continued)

(52) U.S. Cl.
CPC ....... *G01N 33/15* (2013.01); *G01N 2001/022* (2013.01); *G01N 2001/024* (2013.01);
(Continued)

(58) Field of Classification Search
CPC ....... G01N 2001/022; G01N 2001/024; G01N 2001/028; G01N 2001/045;
(Continued)

(56) References Cited

U.S. PATENT DOCUMENTS 3,002,387 A 10/1961 Micheletti
3,067,619 A * 12/1962 Fielding ................... G01N 1/24
73/864.33
(Continued)

FOREIGN PATENT DOCUMENTS

CN 107397903 A 11/2017
CN 108709770 A 10/2018
(Continued)

OTHER PUBLICATIONS

Paret, N. et al, Macromolecular Materials and Engineering 2019, 304, Article 1800599, 15 pages with 22 pages of supporting information. (Year: 2019).*
(Continued)

*Primary Examiner* — Arlen Soderquist
(74) *Attorney, Agent, or Firm* — MARSHALL, GERSTEIN & BORUN LLP

(57) ABSTRACT

The present invention relates to a device and a method for the analytical and/or sensory determination of the release of an active substance or several active substances from a release system. In particular, the present invention relates to a device and a method for determining the release of an active substance or active substances, in particular of an odiferous substance or flavoring or an odiferous substance or flavoring mixture, from a capsule or a precursor. Furthermore, the present invention relates to a device and a method for determining the properties of a release system, in particular of a capsule or a precursor. Ultimately, the present invention relates to the use of the device and method (Continued)

according to the invention for the analytical and/or sensory determination of the release of one or more active substances from a release system.

17 Claims, 7 Drawing Sheets

(51) Int. Cl.
| | |
|---|---|
| *G01N 1/04* | (2006.01) |
| *G01N 1/22* | (2006.01) |

(52) U.S. Cl.
CPC . *G01N 2001/028* (2013.01); *G01N 2001/045* (2013.01); *G01N 2001/2229* (2013.01); *G01N 2001/2241* (2013.01); *Y10T 436/25375* (2015.01); *Y10T 436/25875* (2015.01)

(58) Field of Classification Search
CPC ... G01N 2001/2229; G01N 2001/2241; G01N 2001/22591; G01N 2203/0019; G01N 2203/0021; G01N 2203/0025; G01N 2203/0026; G01N 2203/0028; G01N 2203/0037; G01N 2203/0055; G01N 2203/006; G01N 2203/0067; G01N 2203/0276; Y10T 436/25375; Y10T 436/25875; A61L 9/125
USPC ....... 436/177, 181; 73/23.41, 863.11, 863.82
See application file for complete search history.

(56) References Cited

U.S. PATENT DOCUMENTS

| | | | | | |
|---|---|---|---|---|---|
| 3,321,954 | A | * | 5/1967 | Bailey | G01N 35/021 73/31.03 |
| 3,362,141 | A | * | 1/1968 | Royster, Jr. | G01N 1/04 73/864.33 |
| 3,498,107 | A | | 3/1970 | Kim et al. | |
| 3,941,567 | A | * | 3/1976 | Combaz | G01N 30/12 359/398 |
| 4,111,049 | A | * | 9/1978 | Lerner | G01N 1/24 73/864 |
| 4,909,090 | A | * | 3/1990 | McGown | G01N 1/2214 73/864.33 |
| 5,286,651 | A | * | 2/1994 | Smith | G01N 33/241 850/16 |
| 5,425,263 | A | * | 6/1995 | Davies | G01V 9/007 73/28.06 |
| 5,646,334 | A | * | 7/1997 | Scheppers | G01N 1/26 73/1.06 |
| 5,821,407 | A | * | 10/1998 | Sekiguchi | G01N 11/14 73/54.35 |
| 5,948,360 | A | * | 9/1999 | Rao | G01N 30/24 422/65 |
| 5,959,297 | A | * | 9/1999 | Weinberg | G01N 29/4418 250/288 |
| 6,087,181 | A | * | 7/2000 | Cong | G01N 21/171 436/127 |
| 6,571,610 | B1 | * | 6/2003 | Raffer | G01N 11/14 73/54.23 |
| 6,864,091 | B1 | * | 3/2005 | Wang | G01N 35/109 250/288 |
| 7,364,917 | B2 | * | 4/2008 | Ichimura | G01N 1/2214 422/50 |
| 9,068,954 | B1 | * | 6/2015 | Robinson, Jr. | G01N 31/10 |
| 9,562,880 | B1 | * | 2/2017 | Robinson, Jr. | B01J 35/56 |
| 10,197,558 | B1 | * | 2/2019 | Saaski | C12M 1/34 |
| 2003/0100120 | A1 | * | 5/2003 | Wang | G01N 35/109 436/180 |
| 2003/0155506 | A1 | * | 8/2003 | Motchkine | G01N 1/02 250/288 |
| 2003/0193338 | A1 | * | 10/2003 | Krasnobaev | G01N 27/622 324/464 |
| 2003/0206834 | A1 | * | 11/2003 | Chiao | A61L 9/02 428/905 |
| 2004/0123650 | A1 | * | 7/2004 | Kolosov | G01N 11/14 73/54.35 |
| 2004/0163670 | A1 | * | 8/2004 | Ko | H01L 21/6715 134/25.4 |
| 2004/0203175 | A1 | * | 10/2004 | Li | G01N 30/84 422/503 |
| 2005/0007119 | A1 | * | 1/2005 | Belyakov | G01N 1/22 324/464 |
| 2005/0028819 | A1 | * | 2/2005 | Manne | A61L 9/04 128/204.11 |
| 2005/0058575 | A1 | * | 3/2005 | Ishikawa | G01N 1/2214 422/83 |
| 2005/0153455 | A1 | * | 7/2005 | Lagard | B01F 33/407 436/148 |
| 2006/0070428 | A1 | * | 4/2006 | Bateson | G01N 11/14 73/54.32 |
| 2008/0314166 | A1 | * | 12/2008 | Settles | G01N 1/2226 73/864.35 |
| 2011/0030454 | A1 | * | 2/2011 | Laun | G01N 11/14 73/54.28 |
| 2011/0126643 | A1 | * | 6/2011 | Zhang | G01N 1/24 73/863.11 |
| 2012/0093986 | A1 | * | 4/2012 | Bramoulle | A23K 20/28 426/531 |
| 2013/0299694 | A1 | | 11/2013 | Sato et al. | |
| 2015/0118691 | A1 | * | 4/2015 | De Laat | C12Q 1/56 435/13 |
| 2015/0233796 | A1 | * | 8/2015 | Kashima | G01N 1/2211 250/288 |
| 2016/0257949 | A1 | * | 9/2016 | Sunner | G01N 21/718 |
| 2016/0266022 | A1 | * | 9/2016 | Romirer | G01N 11/14 |
| 2018/0224403 | A1 | | 8/2018 | Ji et al. | |
| 2021/0164873 | A1 | * | 6/2021 | Chu | G01M 99/007 |
| 2022/0003734 | A1 | * | 1/2022 | Yoon | G01N 11/08 |

FOREIGN PATENT DOCUMENTS

| | | | | |
|---|---|---|---|---|
| CN | 108918364 | A | | 11/2018 |
| EP | 0142242 | A1 | | 5/1985 |
| EP | 896213 | A2 | * | 2/1999 |
| EP | 2518485 | A1 | | 10/2012 |
| JP | 63221230 | A | * | 9/1988 |
| JP | 06003209 | A | * | 1/1994 |
| JP | H09-327506 | A | | 12/1997 |
| JP | 2002-371191 | A | | 12/2002 |
| JP | 2015-535731 | A | | 12/2015 |
| JP | 2018178018 | A | | 11/2018 |
| WO | WO-2012/139811 | A1 | | 10/2012 |
| WO | WO-2014-115240 | A1 | | 7/2014 |
| WO | WO-2019201920 | A1 | * | 10/2019 ......... G01M 99/007 |

OTHER PUBLICATIONS

Arctander, "Perfume and Flavor Chemicals," front matter and table of contents, self-publication (1969).

Herrmann, "Controlled Release of Volatiles under Mild Reaction Conditions: From Nature to Everyday Products," Angew. Chem. Int. Ed. 46:5836-5863 (2007).

Translated International Search Report and Written Opinion from International Application No. PCT/EP2019/082811 dated Sep. 21, 2020.

Office Action (and English translation) from Application No. 2022-531359 dated Jul. 31, 2023.

Office Action (and English translation) from Japanese Application No. 2022-531359 dated Nov. 14, 2023.

* cited by examiner

DEVICE AND METHOD FOR THE ANALYTICAL AND SENSORY DETERMINATION OF THE RELEASE OF AN ACTIVE SUBSTANCE FROM A RELEASE SYSTEM

CROSS-REFERENCE TO RELATED APPLICATIONS

This is a U.S. National Phase of International Application PCT/EP2019/082811, filed Nov. 27, 2019.

FIELD OF INVENTION

The present invention relates to a device and a method for the analytical and/or sensory determination of the release of an active substance or several active substances from a release system. In particular, the present invention relates to a device and a method for determining the release of an active ingredient or active ingredients, in particular of an odiferous substance or flavoring or an odiferous substance or flavor mixture, from a capsule or a precursor. Furthermore, the present invention relates to a device and a method for determining the properties of a release system, in particular of a capsule or a precursor. Ultimately, the present invention relates to the use of the device and method according to the invention for the analytical and/or sensory determination of the release of one or more active ingredients from a release system.

A release system in the sense of the invention is a solid preparation, for example particles or capsules, containing one or more active ingredients.

Another example of such release systems are so-called precursors or precursor substances. In such precursors or precursor substances, a chemical or physical impulse, for example a chemical reaction with an agent, temperature, humidity, change in pH, oxygen (oxidation), light, for example UV radiation, enzymes, microorganisms, etc., releases one or more active ingredient(s). For example, in the fragrance production, precursors are molecules with a weak intrinsic odor that release at least one new fragrance molecule when external factors such as temperature, oxygen (oxidation), light, enzymes, microorganisms, chemical reaction (for example, hydrolysis), change in pH or moisture act on them. As a result, over the life span of such a fragrance precursor, new fragrance notes are released again and again, resulting in a slightly varying odor.

By the term "encapsulation" the skilled person generally understands a technique by which finely dispersed solid, liquid or gaseous substances, for example active ingredients, are surrounded by a film-forming shell of polymeric and/or inorganic wall materials and are thus immobilized.

The substances or active ingredients enclosed in the capsules are commonly referred to as the core material.

Depending on the wall or cladding material and the degree of crosslinking, individual properties of the microcapsules can thus be achieved.

The aim here is to protect the active components, known as active ingredients, from reactions with the environment, for example moisture or oxidation, but also reaction with other substances, and/or to be able to release them in a targeted manner at a defined time.

In encapsulation, a distinction is made between capsules of the matrix type or the core/shell type, depending on the phase morphologies. In matrix encapsulation, the active ingredient(s) is/are homogeneously mixed with the shell component ("matrix"), resulting in a particle in which the active ingredient(s) is/are uniformly distributed. Matrix systems are also known as microparticles. Typically, the release of the active ingredient(s) occurs either by diffusion of the active ingredient(s) into the environment or by degradation of the matrix.

In core/shell encapsulation, the active ingredient(s) that form the core are encapsulated with a shell material. A true capsule with one or more shell(s) is created. Usually, a mechanical stress, for example pressure or shear, produces a complete release of the core material. However, it is also possible to selectively release the core material or active ingredient(s) by alternative opening mechanisms, for example temperature, change in pH, UV radiation, microwaves or ultrasound.

In addition to macroscopic particles with diameters in the range up to 1 cm, microcapsules are of particular interest. This is understood by the skilled person to mean spherical particles with a diameter in the range from about 0.0001 to about 5 and preferably 0.005 to 0.5 mm.

According to the invention, the term "microcapsules" refers to particles and aggregates containing an inner space or core filled with a solid, gelled, liquid or gaseous medium and enclosed (encapsulated) by a continuous shell of film-forming polymers. In addition, the microscopic capsules may contain one or more cores distributed in the continuous encapsulation material consisting of one or more layers.

The shell of such microcapsules may consist of natural, semisynthetic or synthetic materials. Natural shell materials are, for example, gum arabic, agar-agar, agarose, maltodextrins, alginic acid or its salts, e.g., sodium or calcium alginate, fats and fatty acids, cetyl alcohol, collagen, chitosan, lecithin, gelatin, albumin, shellac, polysaccharides, such as starch or dextran, polypeptides, protein hydrolysates, sucrose and waxes. Semi-synthetic coating materials include chemically modified celluloses, in particular cellulose esters and ethers, e.g., cellulose acetate, ethyl cellulose, hydroxypropyl cellulose, hydroxypropyl methyl cellulose and carboxymethyl cellulose, and starch derivatives, in particular starch ethers and esters. Synthetic shell materials are, for example polymers such as polyacrylates, polyamides, polyvinyl alcohol, aminoplasts, phenoplasts or polyvinylpyrrolidone.

Depending on the use of different wall and core materials, there are many possible applications.

The preparation of microcapsules has been described in detail in the prior art literature and is accessible by known reactive and non-reactive processes, such as solvent evaporation, precipitation processes, coacervation, interfacial polycondensation, high-pressure encapsulation processes, etc.

Examples of prior art microcapsules include the following commercial products (the shell material is indicated in parentheses in each case): Hallcrest Microcapsules (gelatin, gum arabic), Coletica Thalaspheres (marine collagen), Lipotec Millicapsules (alginic acid, agar-agar), Induchem Unispheres (lactose, microcrystalline cellulose, hydroxypropylmethyl-cellulose); Unicerin C30 (lactose, microcrystalline cellulose, hydroxypropylmethylcellulose), Kobo Glycospheres (modified starch, fatty acid esters, phospholipids), Softspheres (modified agar-agar) and Kuhs Probiol Nanospheres (phospholipids) as well as Primaspheres and Primasponges (chitosan, alginates) and Primasys (phospholipids). As well as capsules made from synthetic polymers Micronal®(BASF), Microcapsules 500 and 560 (Koehler SE), Folco Smart-caps®, Enfinit®Ensensa®.

Due to their properties, capsules, in particular microcapsules, comprising one or more active ingredient(s) are used in the printing industry (e.g., scented coatings), the food industry (e.g., vitamins, flavors, plant extracts, enzymes, microorganisms), the agrochemical industry (e.g., fertilizers, crop protection agents), the feed industry (e.g., minerals, vitamins, enzymes, pharmaceuticals, microorganisms), the pharmaceutical industry, the detergent industry and the cosmetics industry, among others.

Many articles for daily use, such as detergents, fabric softeners, washing powders, liquid detergents, shower gels, shampoos, deodorants, body lotions, etc., are now perfumed with encapsulated odiferous substances or odiferous substance mixtures.

In particular, the capsules, preferably microcapsules, are used for the production of, for example, perfume extracts, eau de parfums, eau de toilettes, shaving waters, eau de colognes, pre-shave products, splash colognes, acidic, alkaline and neutral cleaning agents such as floor cleaners, window glass cleaners, dishwashing detergents, bathroom and sanitary cleaners, scouring milk, solid and liquid toilet cleaners, powder and foam carpet cleaners, liquid laundry detergents, powder laundry detergents, laundry pre-treatment products such as bleaches, softeners and stain removers, fabric softeners, laundry soaps, laundry tablets, disinfectants, surface disinfectants, as well as air fresheners in liquid, gel or solid form, aerosol sprays, waxes and polishes such as furniture polishes, floor waxes, shoe polishes, as well as personal care products, e.g., solid and liquid soaps, shower gels, shampoos, shaving soaps, shaving foams, bath oils, cosmetic emulsions of the oil-in-water, water-in-oil and water-in-oil-in-water type, such as skin creams and lotions, face creams and lotions, sun creams and lotions, after-sun creams and lotions, hand creams and lotions, foot creams and lotions, depilatory creams and lotions, after-shave creams and lotions, tanning creams and lotions, hair care products such as hair sprays, hair gels, setting hair lotions, hair conditioners, permanent and semi-permanent hair dyes, hair shaping products such as cold waves and hair straightening products, hair tonics, hair creams and lotions, deodorants and antiperspirants, e.g., underarm sprays, roll-ons, deodorant sticks, deodorant creams, decorative cosmetic products such as eye shadows, nail polishes, make-ups, lipsticks, mascara, care wipes, baby care wipes, intimate care wipes, refreshing wipes, as well as candles, lamp oils, incense, insecticides, repellents, propellants.

Encapsulation of an active ingredient(s) with a suitable coating material can occur for several reasons:

conversion of liquids into a manageable powder form (e.g., encapsulation of vegetable oils, fats);

time-controlled or delayed release of substances (dosage control, depot effect for drugs, pesticides and fertilizers);

taste, odor and color lamination (e.g., bitter or pungent flavorings);

protection from light, oxidation, heat, acids or bases (e.g., vitamins, flavorings, etc.)

moisture protection of e.g., hygroscopic salts or minerals;

reduction of the evaporation rate of volatile components (e.g., flavorings);

prevention of premature chemical reactions with other mixture components;

better manageability before or during processing (e.g., optimized flow properties, avoidance of fine dust formation);

protection of personnel from harmful or unpleasant materials (chemicals, aroma concentrates); or better dispersibility.

One particular use of microcapsules is in detergents and cleaning agents for the controlled or delayed release of odiferous substances onto textile surfaces. During washing, microcapsules containing an odiferous substance or perfume oil spread over the laundry and adhere to the fabric. When the clothing is worn, the capsules burst due to the friction or pressure that occurs and release the odiferous substance or perfume oil.

The contents of microcapsules can be released in various ways. Four typical mechanisms can be considered:

The capsule walls are mechanically destroyed by crushing or shearing. This mechanism is used, for example, with reaction carbonless paper.

The capsule walls are destroyed by melting of the wall material. According to this mechanism, ingredients such as baking agents or aromas are released, for example, in baking mixtures only during the baking process.

The capsule walls are destroyed by dissolving the wall material. This mechanism is used, for example, in washing powder so that encapsulated ingredients such as enzymes are only released during the washing process.

The capsules remain intact, and the capsule contents are gradually released by diffusion through the capsule wall. According to this mechanism, for example, a slow and uniform release of drug substances in the body can be achieved.

In order to be able to take appropriate measures in the development, manufacture and use of such active ingredient release systems, in particular capsules or precursors, it is important to be aware of the release of active ingredients, for example the concentration of an active ingredient or several active ingredients, the release rate, the release profile of an active ingredient or several active ingredients, etc., as well as their properties, for example mechanical stability of the capsule shell, breaking strength, retardation behavior, etc.

Currently, the determination of the release of an active ingredient or several active ingredients, in particular an odiferous substance or flavoring, from a capsule, in particular from a microcapsule, is carried out by sensory-analytical evaluation using various methods. Specifically trained test persons/panels are used for this purpose.

Descriptive sensory analyses, i.e., the methods of descriptive sensory analysis, are considered the most sophisticated sensory methods due to their diversity and complexity. They are traditionally based on the sensory perception of appropriately qualified persons, yield detailed product profiles, but are time-consuming and expensive. Specially trained testers are used for the tasks within the scope of a classical descriptive analysis, such as identification, description and quantification of objectively sensory perceptible product characteristics. The aim of these procedures is to obtain a detailed product description that can be compared with other products or even translated into product recipes. In addition to the multi-stage sensory procedure, the time-consuming training procedure for tester qualification in classic profile analyses is a particularly significant point of criticism.

Cost and time pressure in innovations as well as ever shorter product life cycles increasingly require faster availability of decision-relevant information. Short-term methods, so-called descriptive rapid methods, can be an alternative in this respect, as they also allow the use of untrained test subjects, but are also associated with information losses.

Although the trend is to standardize sensory evaluation by improving methods or by better training of test subjects, the evaluation remains a subjective assessment that cannot be equated with an objective or standardized method of analysis based on specific criteria.

In sensory analysis, the release of the active ingredients from a release system, in particular from a capsule, is usually carried out by manual friction without standardization for the applied pressure, for example pressure intensity, on the release system, in particular the capsule, so that the result of the release of the active ingredient or active ingredients is subject to strong fluctuations.

The primary task of the present invention was therefore to overcome the above-mentioned problems and to provide a device and a method for carrying out an objective and standardized, i.e., standardized, analytical method which makes it possible to make reproducible, qualitative and/or quantitative statements about the release of an active substance or several active substances, in particular qualitative and/or quantitative statements about the released active substance or substances, and/or about the properties of an active substance release system, in particular a capsule.

In particular, it was the task of the present invention to provide a standardized method for the analytical and/or sensory determination of the release of one or more active ingredients from a release system, in particular one or more active ingredients from a capsule or a precursor.

Furthermore, it was the task of the present invention that the device is simple in design and the method is easy to use as well as variable for a variety of different release systems or active substances.

Ultimately, the present invention sought to ensure that the device could be combined with standard analytical instruments to allow identification and quantification of measurements.

Surprisingly, it was found that the aforementioned tasks are solved by a device and/or a method in which one or more active ingredients are released from a release system 6, preferably from a capsule 6 or a precursor 6, by a physical or chemical impulse, for example pressure and/or friction, the released active ingredient(s) is/are fed to a detection device, and the released active ingredient is ultimately determined analytically.

The procedural advantage is that the device and/or method according to the invention provides an objective analytical method under normalized, i.e., standardized, conditions, which allows, for example, analytical values from different release systems to be compared with each other, and that the release of the active substances can be measured continuously online.

In particular, the device and method according to the invention allow a determination of the concentration of the released active ingredient(s), a determination of the release rate of the active ingredient(s), or a determination of the release profile of one or more active ingredient(s).

On the other hand, the device according to the invention and the method according to the invention allow a determination of the properties of a release system, in particular of a capsule, for example the mechanical stability and the breaking strength of the capsule or the retardation behavior, for example of a capsule after storage for a certain period of time.

With the device according to the invention and the method according to the invention it is furthermore possible to test the distribution and adhesion of a release system, in particular of a capsule (6) or a precursor (6), on a substrate, and/or to analyze the substantivity of an active substance or several active substances after release from the release system (6), in particular from a capsule (6) or a precursor (6), on a substrate; and/or to analyze the influence of physical or chemical factors, for example temperature, light, UV radiation, pH value, on the mechanical stability and breaking strength of a release system and/or to analyze the release of an active substance or several active substances from a release system; and/or to check the release of an active substance or several active substances and the properties of a release system during the development and production of a release system.

SUMMARY OF THE INVENTION

In a first aspect, the present invention relates to a device 1 suitable for analytically and/or sensorially determining the release of one or more active ingredients from a release system 6, in particular one or more active ingredients from a capsule 6 or a precursor 6, and/or for determining the properties of a release system 6, in particular of a capsule 6 or a precursor 6, located on a sample carrier 7 on a support surface 8, comprising:
- (a) a base frame 2;
- (b) an activation device 3 which is connected to the base frame 2 and which is arranged to open or activate the release system 6, in particular the capsule 6 or the precursor 6, and to release the active substance or the multiple active substances contained therein; and
- (c) a detection device 5, set up for analytical determination of the released active ingredient(s), and designed in such a way that the released active ingredient(s) can be fed to the detection device 5.

In a further aspect, the present invention is directed to a method for analytically and/or sensorially determining the release of one or more active ingredients from a release system 6, in particular from a capsule 6 or a precursor 6, and/or for determining the properties of a release system 6, in particular of a capsule 6 or a precursor 6, comprising the following steps:
- (i) providing a release system 6, in particular a capsule 6 or a precursor 6 comprising the one or more active ingredients, on a sample support 7 or on a support surface 8;
- (ii) positioning the activation device 3 with an activator 31 over the release system 6, in particular over the capsule 6 or precursor 6;
- (iii) lowering the activation device 3;
- (iv) releasing the active ingredient or the various active ingredients from the release system 6, in particular from the capsule 6 or the precursor 6, by means of the activator 31;
- (v) collecting and delivering the released agent or agents to a detection device 5; and
- (vi) analytical determination of the active substance or substances released.

Ultimately, the present invention is directed to the use of the device and method of the invention for
- for the analytical and/or sensory determination of the release of an active substance or several active substances, in particular the concentration, the release rate or the release profile from a release system 6, in particular from a capsule 6 or a precursor 6;
- for determining properties, for example the mechanical stability, the breaking strength or the retardation behavior, of a release system 6, in particular a capsule 6 or a precursor 6, in particular the mechanical stability, the breaking strength or the retardation behavior, of capsules 6 made of different capsule materials and different active ingredients;

for analyzing the distribution and adhesion of a release system 6, in particular a capsule 6 or a precursor 6, on a substrate, in particular after washing and drying textiles;

for analyzing the substantivity of one or more active ingredients after release from the release system 6, in particular from a capsule 6 or a precursor 6, on a substrate;

for analyzing the influence of physical or chemical factors, for example temperature, light, UV radiation, pH value, on the mechanical stability and breaking strength of a release system, in particular of a capsule or a precursor 6 and/or on the release of an active ingredient or of several active ingredients from a release system 6, in particular from a capsule 6 or a precursor 6;

for the analytical determination of the release of an active ingredient or several active ingredients and for the determination of the properties of a release system 6, in particular of a capsule 6 or a precursor 6, during the production of the release system 6.

These and other aspects, features and advantages of the present invention will be apparent to those skilled in the art from a study of the following detailed description and claims. In this regard, any feature from any aspect of the invention may in principle be used in any other aspect of the invention. Further, it is understood that the examples herein are intended to describe and illustrate the invention but are not intended to limit the invention and, in particular, the present invention is not limited to these examples.

The term "at least one" as used in the context of the present description refers to one or more, for example, one, two, three, four, five, six, seven, eight, nine, or more. For example, therefore, the term "at least one positioning unit" means that at least one positioning unit is included, but may also include two or more positioning units.

FIGURES

DETAILED DESCRIPTION OF THE INVENTION

Figure 1:
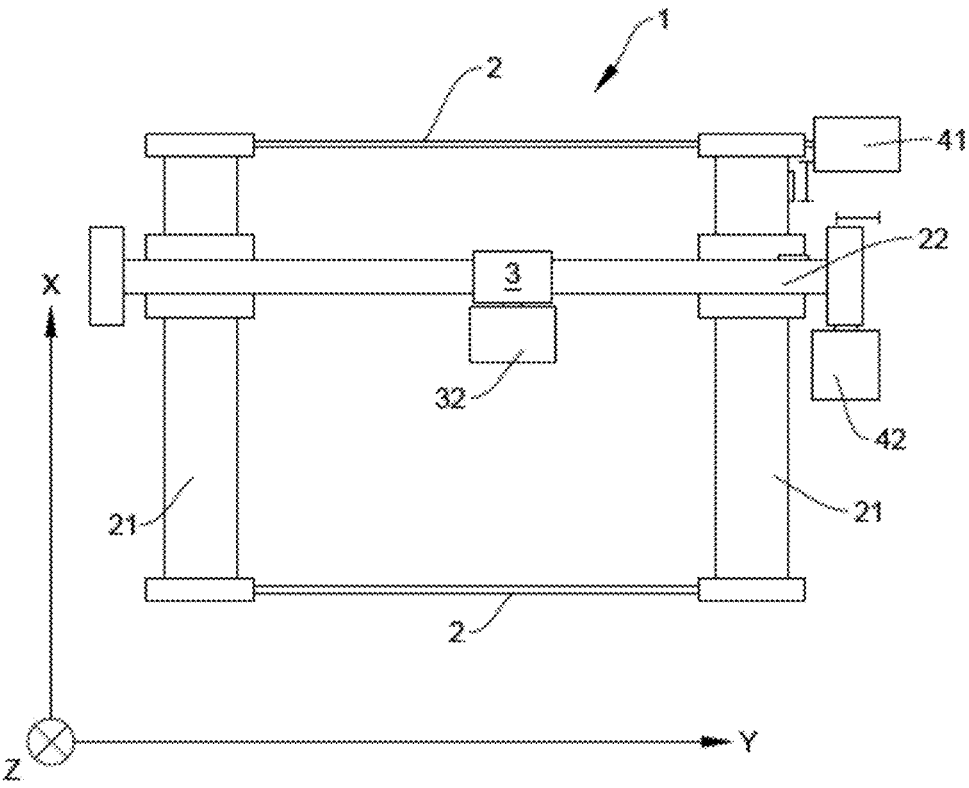
FIG. 1 shows a schematic top view of a preferred variant of the device according to the present invention.
Figure 2:
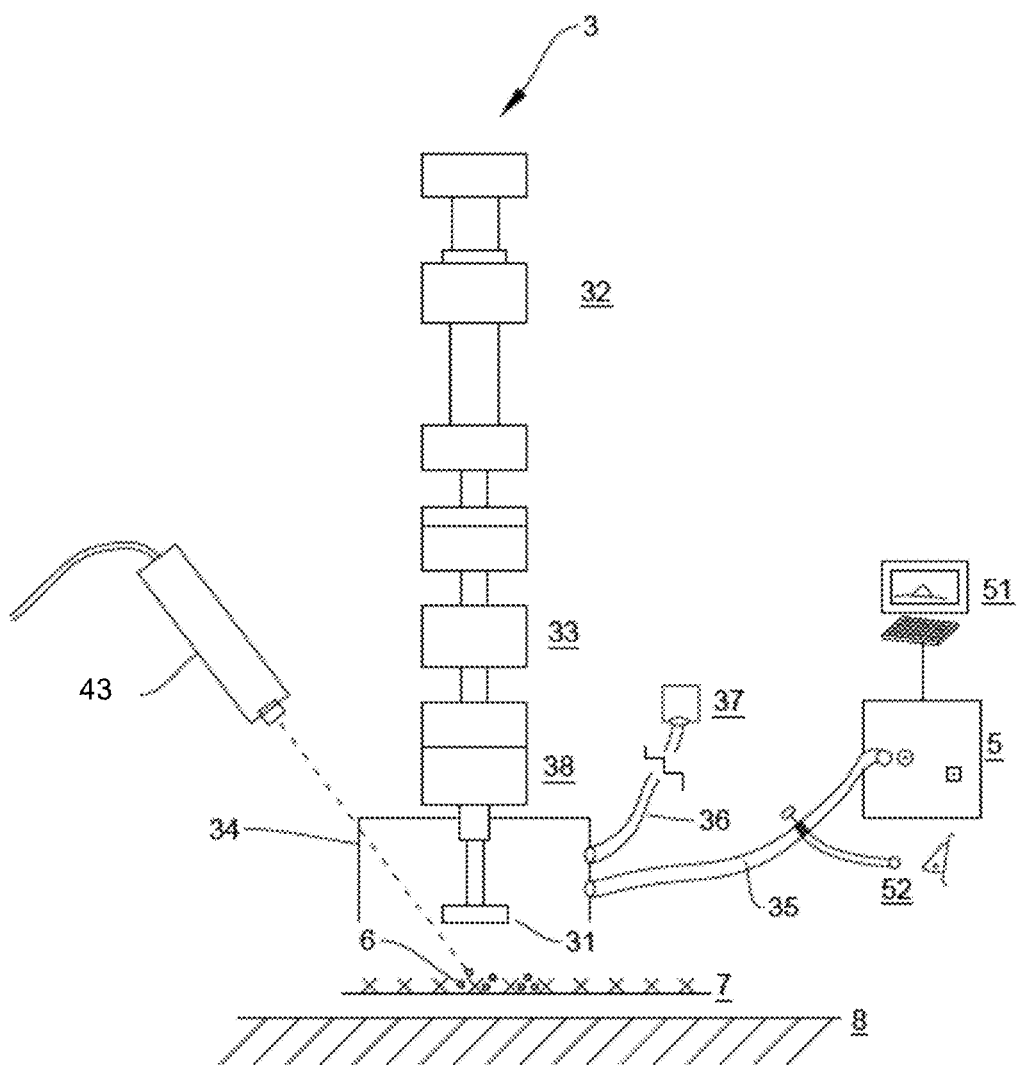
FIG. 2 is a schematic cross-section through a preferred variant of an activation device of the device according to the present invention.
Figure 3:
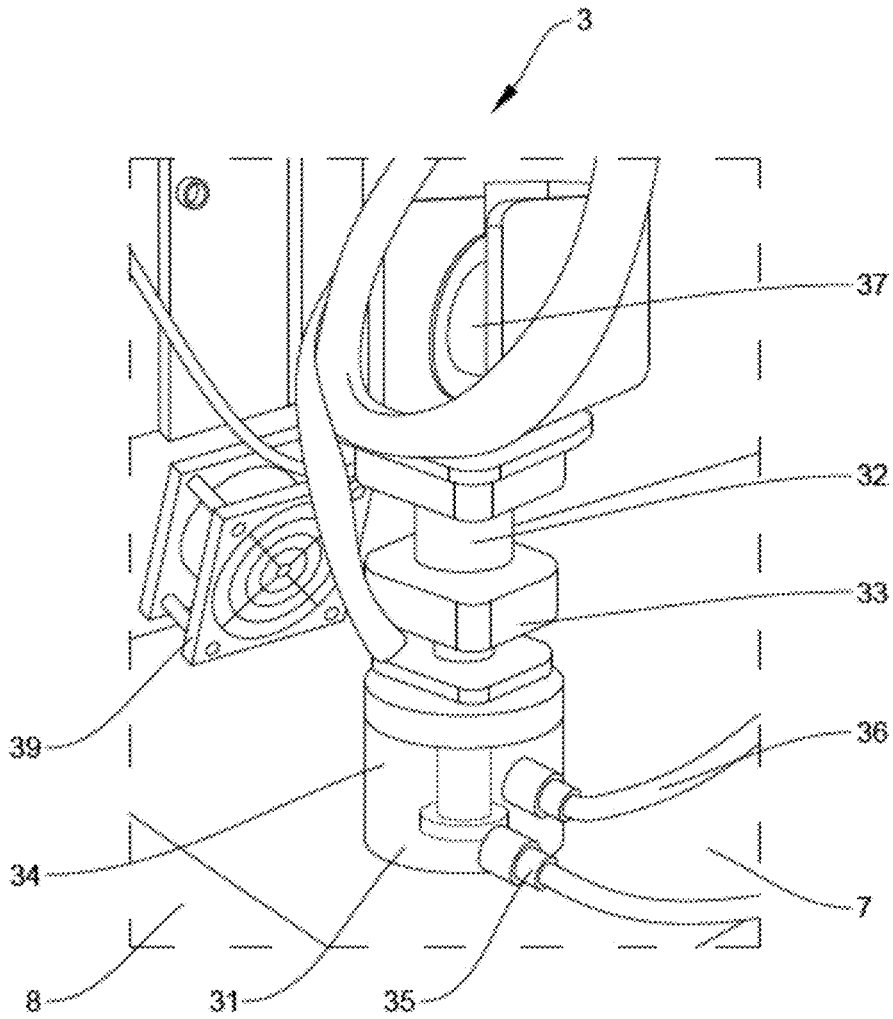
FIG. 3 is a detailed perspective view of a preferred variant of the device according to the present invention.
Figure 4:
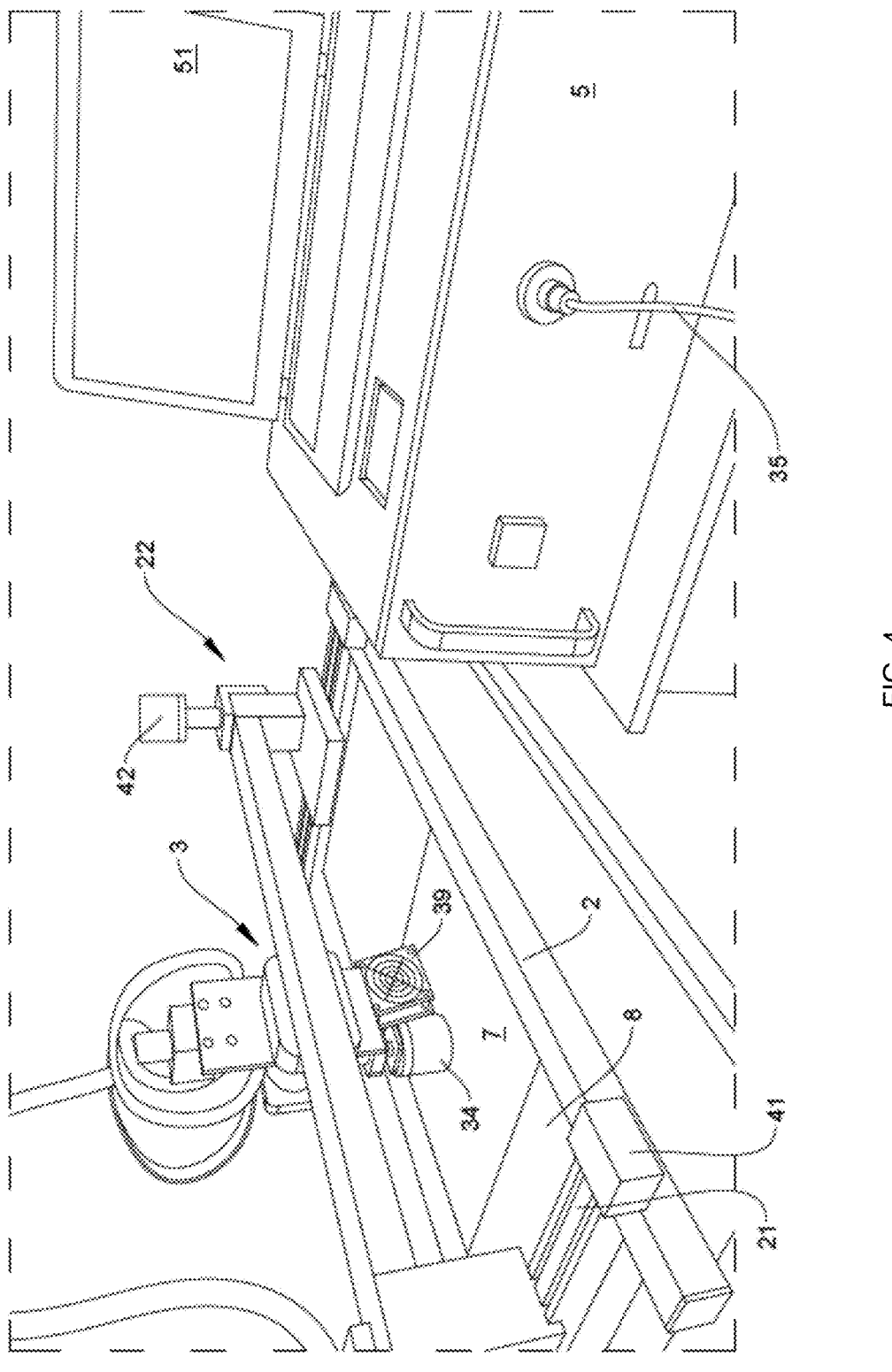
FIG. 4 is a perspective view of a preferred variant of the device in overall view with detection system and feed lines according to the invention.

In the following, the device according to the invention, variants of the device as well as preferred embodiments thereof are described in more detail with reference to the attached FIGS. 1 to 4.

The device 1 for analytical and/or sensory determination is not to be understood merely for analytical determination of the release of one or more active ingredients from a capsule, but is configured generally for analytical and/or sensory determination of the release of one or more active ingredients from a release system comprising or including an active ingredient.

A release system in the context of the present invention is understood to be a solid preparation, for example particles or capsules, containing one or more active ingredients. A preferred release system is a capsule, preferably a microcapsule, of the matrix type or the core/shell type. In matrix encapsulation, the active ingredient(s) is/are homogeneously mixed with the shell component ("matrix") to form a particle in which the active ingredient(s) is/are uniformly distributed. Typically, the release of the active ingredient(s) from this type of capsule occurs either by diffusion of the active ingredient(s) into the environment or by the degradation rate of the matrix. In core-shell encapsulation, the active ingredient(s) that form the core are encapsulated with a shell material. A true capsule with one or more shell(s) is formed. Usually, a mechanical stress, for example pressure or shear, produces a complete release of the core material. However, it is also possible to selectively release the core material by alternative opening mechanisms, for example temperature, pH work, UV light, microwaves or ultrasound.

In the context of the present invention, a suitability of the device 1 according to the invention for the analytical determination of the release of an active ingredient from a capsule, such as from hard-shelled capsules, soft-shelled capsules, macrocapsules, microcapsules, capsule slurries, capsule emulsions, is particularly preferred.

A release system in the context of the present invention also refers to a precursor or precursor substance. In such a precursor or precursor substance, a chemical or physical stimulus, for example, temperature, oxygen (oxidation), light, enzymes, microorganisms, chemical reaction (for example, hydrolysis), change in pH or moisture, etc., one or more active ingredients are released. Precursors used according to the invention are, for example, odiferous substances with a weak inherent odor that release at least one new fragrance molecule when they come into contact with external factors such as light, water or oxygen. As a result, new fragrance notes are repeatedly released over the life span of a fragrance, resulting in a slightly varying odor.

In the context of the present invention, the term "release system" preferably includes capsules, in particular microcapsules, as well as precursors or precursor substance. The terms "release system", "capsule", "microcapsule", "precursor or precursor substance" are used in the following description equally next to each other and interchangeably with each other in such a way that one term includes the other term and vice versa. The terms "capsule" and "microcapsule" include both a matrix-type capsule and a core/shell-type capsule.

In a first aspect, the present invention consequently relates to a device 1 for analytical and/or sensory determination of the release of one or more active ingredients from a release system 6, preferably one or more active ingredients from a capsule 6 or a precursor.

By release is meant the release or generation of an active ingredient from the formulation, i.e., from the release system 6, preferably the capsule 6 or the precursor 6.

Analytical determination is generally understood to mean a qualitative (identification of the active ingredient) and/or quantitative (amount of the active ingredient) analysis of an active ingredient or active ingredients released from the release system 6, in particular of one or more active ingredients released from a capsule 6 or a precursor 6. By means of the analytical determination, the concentration of the released active ingredient or active ingredients as well as the release rate, i.e., the release of the active ingredient or active ingredients over time, can be determined.

The determination of the release rate involves measuring how, i.e., with what intensity and/or in what concentration, the active ingredient or the multiple active ingredients are released from the capsule over time.

In addition, the analytical determination can also be used to determine the release profile, i.e., rapid or delayed release, of an active ingredient or several active ingredients, both qualitatively and quantitatively. The determination of the release profile is particularly important for mixtures of active ingredients, for example perfume oils, odiferous substance mixtures or flavoring mixtures. By means of the release profile, it can be determined how, i.e., with what intensity and/or in what concentration over time, the individual components of an odiferous substance mixture or flavoring mixture are released from the release system, in particular from a capsule 6 or from a precursor 6.

Furthermore, the device 1 is configured for determining the properties of a release system 6, in particular of a capsule 6. By determination of the properties of a release system is meant an analysis of the functional properties, such as mechanical stability, breaking strength or retardation behavior, in particular after storage over a certain period of time, etc. of the release system or capsule.

By analyzing the released active ingredient(s), information can be obtained about the concentration of the released active ingredient, about the speed of release of the active ingredient (rapid vs. sustained release), about the release profile, for example of an active ingredient mixture, or about how stable the capsule shell is, which burst behavior (break-up behavior) the capsule shell exhibits, which retardation properties the capsule shell has, for example after storage of the release system for a certain period of time, etc.

The material or contained core material or active substance distributed in the matrix in the release system 6, preferably the capsule 6, is a solid, liquid or gaseous substance. Preferably, the core material of the release system 6 is a volatile substance that is volatile at room temperature.

The selection of active ingredients used in the release system described above is essentially based on the intended use of the release system.

Preferably, in the release system 6, preferably the capsule 6, are used active ingredients from the fields of detergents and cleaning agents, adhesives, coating compositions such as paints and varnishes, binders, materials such as plastics, paper, textiles, lubricants, construction materials, dyes, organic and inorganic powders, pigment dispersions, phase transition materials, flame retardants agrochemicals, but also active ingredients from cosmetic and pharmaceutical fields.

Preferably, the release system 6, preferably the capsule 6, contains at least one active ingredient selected from the group consisting of: odiferous substances, flavorings, perfume oils, odiferous substance mixtures, aromas, vitamins, minerals, antioxidants, anthocyanins, coenzyme IO, adhesives, mineral oils, waxes and fats, biocides, fungicides, herbicides, pesticides, insecticides, fertilizers, disperse dyes and dye solutions or monomers for the synthesis of plastics.

Preferably, the one or more active ingredient(s) is/are odiferous substances, flavorings, perfume oils, odiferous substance mixtures or aromas. These active ingredients are predominantly volatile substances that are volatile at room temperature.

The preferably used odiferous substances or flavorings or odiferous substance mixtures or flavoring mixtures comprising two, three, four, five or even much more further odiferous or flavoring components are selected from the group consisting of: (1) hydrocarbons; (2) aliphatic alcohols; (3) aliphatic aldehydes and their acetals; (4) aliphatic ketones and their oximes; (5) aliphatic sulfur-containing compounds; (6) aliphatic nitriles; (7) esters of aliphatic carboxylic acids; (8) acyclic terpene alcohols; (9) acyclic terpene aldehydes and ketones; (10) cyclic terpene alcohols; (11) cyclic terpene aldehydes and ketones; (12) cyclic alcohols; (13) cycloaliphatic alcohols; (14) cyclic and cycloaliphatic ethers; (15) cyclic and macrocyclic ketones; (16) cycloaliphatic aldehydes; (17) cycloaliphatic ketones; (18) esters of cyclic alcohols; (19) esters of cycloaliphatic alcohols; (20) esters of cycloaliphatic carboxylic acids; (21) araliphatic alcohols; (22) esters of araliphatic alcohols and aliphatic carboxylic acids; (23) araliphatic ethers; (24) aromatic and araliphatic aldehydes; (25) aromatic and araliphatic ketones; (26) aromatic and araliphatic carboxylic acids and their esters; (27) nitrogen-containing aromatic compounds; (28) phenols, phenyl ethers and phenyl esters; (29) heterocyclic compounds; (30) lactones; and any mixtures thereof.

The selection of odiferous substances or flavorings is very comprehensive in this regard; corresponding substances can be found, for example, in "S. Arctander, Perfume and Flavor Chemicals, Volumes I and II, Montclair, N. J., 1969, self-published" or "H. Surburg and J. Panten, Common Fragrance and Flavor Materials, 6th edition, Wiley-VCH, Weinheim, 2016."

In detail, the following may be mentioned:

Extracts from natural raw materials: This group represents essential oils, concretes, absolutes, resins, resinoids, balsams, tinctures such as Ambergris tincture; Amyris oil; Angelica seed oil; Angelica root oil; Anise oil; Valerian oil; Basil oil; Tree moss absolute; Bay oil; Mugwort oil; Benzo resin; Bergamot oil; Beeswax absolute; Birch tar oil; Bitter almond oil; Savory oil; Bucco leaf oil; Cabreuva oil; Cade oil; Calamus oil; Camphor oil; Cananga oil; Cardamom oil; Cascarilla oil; Cassia oil; Cassie-absolute; Castoreum-absolute; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolute; Oak moss absolute; Elemi oil; Tarragon oil; Eucalyptus citriodora oil; Eucalyptus oil; Fennel oil; Spruce needle oil; Galbanum oil; Galbanum resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; Calamus oil; Chamomile oil blue; Chamomile oil Roman; Carrot seed oil; Cascarilla oil; Pine needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; Litsea cubeba oil; Bay leaf oil; Mace oil; Marjoram oil; Mandarin oil; Masso bark oil; Mimosa absolute; Musk grain oil; Musk tincture; Muscat oil; Myrrh absolute; Myrrh oil; Myrtle oil; Clove leaf oil; Clove flower oil; Neroli oil; Olibanum absolute; Olibanum oil; Opopanax oil; Orange flower absolute; Orange oil; Origanum oil; Palmarosa oil; Patchouli oil; Perilla oil; Peru balsam oil; Parsley leaf oil; Parsley seed oil; Petitgrain oil; Peppermint oil; Pepper oil; Allspice oil; Pine oil; Poley oil; Rose absolute; Rosewood oil; Rose oil; Rosemary oil; Sage oil Dalmatian; Sage oil Spanish; Sandalwood oil; Celery seed oil; Spicy lavender oil; Star anise oil; Styrax oil; Tagetes oil; Fir needle oil; Tea tree oil; Turpentine oil; Thyme oil; Tolu balsam; Tonka absolute; Tuberose absolute; Vanilla extract; Violet leaf absolute; Verbena oil; Vetiver oil; Juniper berry oil; Wine yeast oil; Wormwood oil; Wintergreen oil; Ylang oil; hyssop oil; Civet absolute; Cinnamon leaf oil; Cinnamon bark oil, and fractions thereof, or ingredients isolated therefrom.

Single odiferous substances: single odiferous substances can be divided into a variety of classes, namely:

hydrocarbons, such as 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols such as hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methylenehep-tan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals such as hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethyl acetal; 1,1-dimethoxy-2,2,5-trimethyl-4-hexene; citronellyloxyacetaldehyde; 1-(1-methoxy-propoxy)-(E,Z)-3-hexene;

aliphatic ketones and their oximes such as 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

aliphatic sulfur-containing compounds such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate; 4-methyl-2-pentyl crotonate;

acyclic terpene alcohols such as citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

acyclic terpene aldehydes and ketones such as geranial; neral; citronellal; 7-hydroxy-3,7-dimethyloctanal; 7-methoxy-3,7-dimethyloctanal; 2,6,10-trimethyl-9- undecenal; geranylacetone; and the dimethyl and diethylacetals of geranial, neral, 7-hydroxy-3,7-dimethyloctanal;

cyclic terpene alcohols such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerianates, pentanoates, hexanoates, crotonates, tiglinates and 3-methyl-2-butenoates;

cyclic terpene aldehydes and ketones such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-on; 1,3,4,6,7,8a-hexahydro-1,1,5,5-tetramethyl-2H-2,4a-methanonaphthalen-8(5H)-on; 2-methyl-4-(2,6,6-trimethyl-1-cyclohexen-1-yl)-2-butenal; nootkatone; dihydroneootkatone; 4,6,8-megastigmatrien-3-one; alpha-sinensal; beta-sinensal; acetylated cedarwood oil (methyl cedryl ketone);

cyclic alcohols such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan ; 1,5,9-trimethyl-13-oxabicyclo[10.1.0] trideca-4,8-diene; rose oxide; 2-(2, 4-dimethyl-3-cyclohexen-1-yl)-5-methyl-5-(1-methylpropyl)-1,3-dioxane;

cyclic and macrocyclic ketones such as 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones such as 1-(3,3-dimethylcyclo-
hexyl)-4-penten-1-on; 2,2-dimethyl-1-(2,4-dimethyl-3-
cyclohexen-1-yl)-1-propanon; 1-(5,5-dimethyl-1-cy-
clohexen-1-yl)-4-penten-1-on; 2,3,8,8-tetramethyl-1,2,
3,4,5,6,7,8-octahydro-2-naphthalenyl methyl ketone;
methyl 2,6,10-trimethyl 2,5,9-cyclododecatrienyl
ketone; tert-butyl-(2,4-dimethyl-3-cyclohexen-1-yl)ke-
tone;
esters of cyclic alcohols such as 2-tert-butyl cyclohexyl
acetate; 4-tert-butyl cyclohexyl acetate; 2-tert-pentyl
cyclohexyl acetate; 4-tert-pentyl cyclohexyl acetate;
3,3,5-trimethyl cyclohexyl acetate; decahydro-2-naph-
thyl acetate; 2-cyclopentyl cyclopentyl crotonate;
3-pentyl tetrahydro-2H-pyran-4-yl acetate; decahydro-
2,5,5,8a-tetramethyl-2-naphthyl acetate; 4,7-methano-
3a,4,5,6,7,7a-hexahydro-5, resp. 6-indenyl acetate; 4,7-
methano-3a,4,5,6,7,7a-hexahydro-5, or 6-indenyl
propionate; 4,7-methano-3a,4,5,6,7,7a-hexahydro-5, or
6-indenyl isobutyrate; 4,7-methanooctahydro-5, or
6-indenyl acetate;
esters of cycloaliphatic alcohols such as 1-cyclohexyl-
ethyl crotonate;
esters of cycloaliphatic carboxylic acids such as allyl
3-cyclohexyl propionate; allyl cyclohexyloxy acetate;
cis and trans methyl dihydrojasmonate; cis and trans
methyl jasmonate; methyl 2-hexyl-3-oxocyclopentane
carboxylate; ethyl 2-ethyl-6,6-dimethyl-2-cyclohexen-
ecarboxylate; ethyl 2,3,6,6-tetramethyl-2-cyclohexen-
ecarboxylate; ethyl 2-methyl-1,3-dioxolane-2-acetate;
araliphatic alcohols such as benzyl alcohol; 1-phenylethyl
alcohol; 2-phenylethyl alcohol; 3-phenyl propanol;
2-phenyl propanol; 2-phenoxyethanol; 2,2-dimethyl-3-
phenyl propanol; 2,2-dimethyl-3-(3-methylphenyl)pro-
panol; 1,1-dimethyl-2-phenylethyl alcohol; 1,1-dim-
ethyl-3-phenylpropanol; 1-ethyl-1-methyl-3-
phenylpropanol; 2-methyl-5-phenylpentanol;
3-methyl-5-phenylpentanol; 3-phenyl-2-propen-1-ol;
4-methoxybenzyl alcohol; 1-(4-isopropylphenyl)etha-
nol;
esters of araliphatic alcohols and aliphatic carboxylic
acids such as benzyl acetate; benzyl propionate; benzyl
isobutyrate; benzyl isovalerate; 2-phenylethyl acetate;
2-phenylethyl propionate; 2-phenylethyl isobutyrate;
2-phenylethyl isovalerate; 1-phenylethyl acetate;
alpha-trichloromethyl benzyl acetate; alpha,alpha-dim-
ethylphenyl ethyl acetate; alpha,alpha-dimethylphenyl
ethyl butyrate; cinnamyl acetate; 2-phenoxyethyl
isobutyrate; 4-methoxybenzyl acetate;
araliphatic ethers such as 2-phenylethyl methyl ether;
2-phenylethyl isoamyl ether; 2-phenylethyl-1-ethoxy-
ethyl ether; phenylacetaldehyde dimethyl acetal; phe-
nylacetaldehyde diethyl acetal; hydratropaaldehyde
dimethyl acetal; phenylacetaldehyde glycerol acetal;
2,4,6-trimethyl-4-phenyl-1,3-dioxane; 4,4a,5,9b-tetra-
hydroindeno[1,2-d]-m-dioxin; 4,4a,5,9b-tetrahydro-2,
4-dimethylindeno[1,2-d]-m-dioxin;
aromatic and araliphatic aldehydes such as benzaldehyde;
phenylacetaldehyde; 3-phenylpropanal; hydratropaal-
dehyde; 4-methylbenzaldehyde; 4-methylphenylacetal-
dehyde; 3-(4-ethylphenyl)-2,2-dimethylpropanal;
2-methyl-3-(4-isopropylphenyl)propanal; 2-methyl-3-
(4-tert.-butylphenyl)propanal; 2-methyl-3-(4-
isobutylphenyl)propanal; 3-(4-tert.-butylphenyl)propa-
nal; cinnamaldehyde; alpha-butylcinnamaldehyde;
alpha-amylcinnamaldehyde; alpha-hexylcinnamalde-
hyde; 3-methyl-5-phenylpentanal; 4-methoxybenzalde-
hyde; 4-hydroxy-3-methoxybenzaldehyde; 4-hydroxy-

14

3-ethoxybenzaldehyde; 3,4-
methylenedioxybenzaldehyde; 3,4-
dimethoxybenzaldehyde; 2-methyl-3-(4-
methoxyphenyl)propanal; 2-methyl-3-(4-
methylenedioxyphenyl)propanal;
aromatic and araliphatic ketones such as acetophenone;
4-methylacetophenone; 4-methoxyacetophenone;
4-tert.-butyl-2,6-dimethylacetophenone; 4-phenyl-2-
butanone; 4-(4-hydroxyphenyl)-2-butanone; 1-(2-
naphthalenyl)ethanone; 2-benzofuranylethanone;
(3-methyl-2-benzofuranyl)ethanone; benzophenone;
1,1,2,3,6-hexamethyl-5-indanylmethyl ketone; 6-tert.-
Butyl-1,1-dimethyl-4-indanyl methyl ketone; 1-[2,3-
dihydro-1,1,2,6-tetramethyl-3-(1-methylethyl)-1H-5-
indenyl]ethanone; 5',6',7',8'-tetrahydro-3',5',5',6',8',8'-
hexamethyl-2-acetonaphthone;
aromatic and araliphatic carboxylic acids and their esters
such as benzoic acid; phenylacetic acid; methyl ben-
zoate; ethyl benzoate; hexyl benzoate; benzyl benzoate;
methyl phenyl acetate; ethyl phenyl acetate; geranyl
phenyl acetate; phenyl ethyl phenyl acetate; methyl
cinnamate; ethyl cinnamate; benzyl cinnamate; phenyl
ethyl cinnamate; cinnamyl cinnamate; allyl phenoxy
acetate; methyl salicylate; isoamyl salicylate; hexyl
salicylate; cyclohexyl salicylate; cis-3-hexenyl salicy-
late; benzyl salicylate; phenyl ethyl salicylate; methyl
2,4-dihydroxy-3,6-dimethylbenzoate; ethyl 3-phenyl
glycidate; ethyl 3-methyl-3-phenyl glycidate;
nitrogen-containing aromatic compounds such as 2,4,6-
trinitro-1,3-dimethyl-5-tert-butylbenzene; 3,5-dinitro-
2,6-dimethyl-4-tert.butylacetophenone; cinnamic acid
nitrile; 3-methyl-5-phenyl-2-pentenoic acid nitrile;
3-methyl-5-phenylpentanoic acid nitrile; methyl
anthranilate; methyl N-methyl anthranilate; Schiff
bases of methyl anthranilate with 7-hydroxy-3,7-dim-
ethyloctanal, 2-methyl-3-(4-tert.-butylphenyl)propanal
or 2,4-dimethyl-3-cyclohexenecarbaldehyde; 6-isopro-
pylquinoline; 6-isobutylquinoline; 6-sec-butylquino-
line; 2-(3-phenylpropyl)pyridine; indole; scatole;
2-methoxy-3-isopropylpyrazine; 2-isobutyl-3-
methoxypyrazine;
phenols, phenyl ethers and phenyl esters such as tarragol;
anethole; eugenol; eugenyl methyl ether; isoeugenol;
isoeugenyl methyl ether; thymol; carvacrol; diphenyl
ether; beta-naphthyl methyl ether; beta-naphthyl ethyl
ether; beta-naphthyl isobutyl ether; 1,4-dimethoxyben-
zene; eugenyl acetate; 2-methoxy-4-methylphenol;
2-ethoxy-5-(1-propenyl)phenol; p-cresyl phenyl
acetate;
heterocyclic compounds such as 2,5-dimethyl-4-hydroxy-
2H-furan-3-one; 2-ethyl-4-hydroxy-5-methyl-2H-furan-3-
one; 3-hydroxy-2-methyl-4H-pyran-4-one; 2-ethyl-3-hy-
droxy-4H-pyran-4-one;
lactones such as 1,4-octanolide; 3-methyl-1,4-octanolide;
1,4-nonanolide; 1,4-decanolide; 8-decene-1,4-olide;
1,4-undecanolide; 1,4-dodecanolide; 1,5-decanolide;
1,5-dodecanolide; 4-methyl-1,4-decanolide; 1,15-pen-
tadecanolide; cis and trans-11-pentadecene-1,15-olide;
cis and trans 12-pentadecene-1,15-olide; 1,16-hexade-
canolide; 9-hexadecene-1,16-olide; 10-oxa-1,16-hexa-
decanolide; 11-oxa-1,16-hexadecanolide; 12-oxa-1,16-
hexadecanolide; ethylene-1,12-dodecanedioate;
ethylene-1,13-tridecanedioate; coumarin; 2,3-dihydro-
coumarin; octahydrocoumarin;
as well as any mixtures of the aforementioned odiferous
substances or flavorings.

Also, suitable and preferred as active ingredients are so-called precursor compounds or precursors, preferably odiferous precursor compounds or odiferous precursors. This class of compounds is about compounds which release a desired odor and/or fragrance molecule by breaking a chemical bond, for example by chemical reaction, temperature, moisture, change in pH, oxygen (oxidation), light, in particular UV light, enzymes or microorganisms. Typically, to form an odiferous precursor, a desired odiferous raw material is chemically combined with a carrier, preferably a slightly volatile or moderately volatile carrier. The combination results in a less volatile and more hydrophobic odiferous precursor with improved substantivity on fabrics. The odiferous substance is subsequently released by breaking the bond between the odiferous raw material and the carrier, for example, by a change in pH (e.g., due to perspiration during wear), humidity, heat, and/or sunlight during storage or drying on a clothesline.

Such odiferous precursors are described, for example, in *Herrmann, Andreas, Controlled release of volatiles under mild reaction conditions: from nature to everyday products, Angew. Chem., Int. Ed.,* 2007, 46, pages 2-30, the disclosure of which is incorporated by reference in its entirety in the present application.

Preferably, the device 1 according to the present invention comprises a base frame 2. The base frame may have any shape and construction adapted to receive an activation device (3).

In a preferred variant of the device according to the invention, the base frame comprises at least one X-axis 21 and one Y-axis 22. In a further preferred variant, the base frame 2 comprises two legs which run parallel to one another. The X-axis 21 is supported, preferably at a 90° angle, on the base frame and is arranged to move an activation device 3 horizontally and in the X-direction relative to the support surface 8 or the plane on which the sample to be analyzed lies. Preferably, the device according to the present invention has two X-axes 21 that are spaced apart and parallel to each other on the base frame.

On the two X-axes 22, in turn, a Y-axis 22 is supported, preferably at a 90°-angle, which is set up to move an activation device 3 horizontally and in the Y-direction relative to the support surface 8 or the plane on which the sample to be analyzed lies.

By means of the two X-axes 21 and the Y-axis 22, the activation device 3 can be set to predetermined coordinates of the support surface 8 on which the sample carrier 7 or the directly sample lies, or moved in the direction towards the sample 6 to be analyzed and positioned exactly above the sample.

The device 1 for analytical and/or sensory determination of one or more active ingredients from a release system 6, in particular from a capsule 6 or a precursor 6, according to the first aspect of the present invention further comprises an activation device 3. The activation device 3 serves to open, for example break open or activate the release system 6, in particular the capsule 6 or the precursor 6, in order to release the active ingredient or the plurality of active ingredients from the release system. The activation device of the device according to the invention is preferably arranged on the base frame 2, in particular on the Y-axis 22, and connected thereto. For movement and positioning with respect to the sample 6, the activation device 3 is attached to the base frame 2 so as to be freely movable, in particular three-dimensionally.

The movement and positioning of the activation device 3 horizontally and in X and Y position relative to the sample carrier 7 or the support surface 8 on which the analyzing sample 6, i.e., the release system 6, lies, is achieved by means of X/Y positioning units (41; 42). The positioning units are either a drive, by means of which the coordinates of the activation device 3 can be set manually, or can be set by means of an electric motor controlled by an EDP. Preferably, the positioning unit is an electric motor which controls the coordinates of the sample 6 to be analyzed by means of an EDP control and positions the activation device 3 above the sample 6 to be analyzed.

For the analytical and/or sensory determination, the sample 6, i.e., the active substance release system 6 to be analyzed, preferably the capsule 6 to be analyzed or the precursor 6 to be analyzed, is located on a sample carrier 7, which in turn is preferably located on a support surface 8. The support surface 8 is usually a surface on which the device 1 according to the invention is also located. In an alternative variant, the sample 6, i.e., the active substance release system to be analyzed, preferably the capsule 6 to be analyzed or the precursor 6 to be analyzed, can also be located directly on the support surface 8. Both the sample carrier 7 and the support surface 8 may also be part of the device 1.

The sample carrier 7 or the support surface 8 on which the sample 6 to be analyzed is located is preferably arranged within the base frame 2 of the device according to the invention.

The support surface 8 is preferably a mat with a smooth surface, preferably made of plastic. Preferably, the support surface 8 is a rubber mat that prevents the sample carrier 7 from slipping during the analysis process.

For example, in order to test the distribution or adhesion of an active ingredient release system on a particular substrate, the sample carrier 7 can also be a fabric, for example clothing, linen, etc. made of cotton, linen, wool, viscose, polyacrylic, polyamide, polyester, or another organic or inorganic substrate or its surface, for example tiles, linoleum, wood, glass, metal, hair, etc., or can be a fiber blanket.

In the alternative variant in which the sample 6 is located directly on the supporting surface 8, for example in the case of a floor cleaning composition with an encapsulated active ingredient 6 or a precursor 6, the device according to the invention for analyzing the active ingredient can be positioned directly above the supporting surface and the analysis can be carried out on the surface of the supporting surface 8. In such a case, the support surface 8 can also be a fabric, for example clothing, linen, etc. made of cotton, linen, wool, viscose, polyacrylic, polyamide, polyester, or another organic or inorganic substrate or its surface, for example tiles, linoleum, wood, glass, metal, hair, etc., or can be a fiber blanket.

Furthermore, according to the first aspect of the present invention, the device for analytical and/or sensory determination of one or more active ingredients from a release system, in particular from a capsule 6 or a precursor 6, comprises a detection device or an analysis device 5 for analytical determination of the released active ingredient or the plurality of released active ingredients. The detection device or analysis device 5 is configured such that the released active agent or the plurality of released active agents can be supplied to the detection device 5 via a detection line 35.

The detection device or analyzer system 5 is such measuring equipment that enables a qualitative and/or quantitative analysis of the released active substance or substances.

The detection device or analysis device 5 is preferably selected from the group consisting of gas chromatograph (GC), gas chromatograph/mass spectrometer (GC/MS), ion mobility spectrometry (IMS), FAIMS (high field asymmetric waveform ion mobility spectrometry), GC-FAIMS, and GC-MS-FAIMS, or combinations of the aforementioned measurement devices.

Preferably, the detection device or analysis device 5, IMS (ion mobility spectrometry), FAIMS (high field asymmetric waveform ion mobility spectrometry), GC-FAIMS and GC-MS-FAIMS or a combination of the aforementioned measuring devices is used for analysis.

The most preferred detection device or analysis device is FAIMS (high field asymmetric waveform ion mobility spectrometry). FAIMS allows detection and analysis of volatile chemical species directly from a gas stream or from the gas phase over a liquid or solid sample. There are two mechanisms for delivering the sample to the FAIMS unit: single sampling or continuous sampling. In single sampling, a defined volume of the gaseous analyte, i.e., the released drug, is collected or adsorptively enriched in an upstream step and fed to the FAIMS. In continuous sampling, the gaseous analyte, i.e., the released active ingredient, is continuously fed to the FAIMS by means of a carrier gas. Preferably, the sampling is performed continuously, which allows the analytical determination of the released active ingredient(s) to be performed in real time. This enables an analytical determination of the real-time release, which is particularly advantageous when determining the release of odiferous substance or flavoring mixtures.

In addition, the device 1 according to the invention makes it possible to bind the released active ingredient or the multiple released active ingredients to an adsorbent, for example in a Tenax tube, in order to concentrate them and subsequently measure them by means of GC-MS (dynamic headspace method). In the dynamic headspace technique, the active ingredient(s) released during the measurement is/are directed via a continuous air flow, generated for example by the FAIMS or for which an additional external pump is used, or an inert gas onto a suitable adsorbent material, for example in a Tenax tube, or into a cold trap. For this purpose, the adsorbent-containing glass tube can either be directly incorporated into the air flow from the CBA, or the active ingredient(s) is/are first (if the air flow is too high for the direct method) passed into a closed container (e.g., a plastic bag), and then the active ingredient(s) is/are passed onto the adsorbent with a lower air flow. The Tenax tube (adsorbent) or trap is then heated and the enriched analytes pass to the FAIMS, for example, or onto the column for gas chromatographic analysis.

In a preferred variant, the detection device or analysis device 5 has an alternative output for an olfactometer and/or an olfactory detection port (ODP) (sniffing port system) 52, with which a sensory determination of the released active substance or substances is possible at the same time, so that a sensory analysis of the active substance can be carried out in addition to the qualitative and/or quantitative analysis. Such a combination allows a correlation to be established between the analytical and sensory determination.

In the device according to the invention, the sniffing port system can be arranged both in front of the detection device 5 and behind the detection device 5. The arrangement of the sniffing port system behind the detection device 5 is particularly advantageous if the detection device 5 is a FAIMS or an IMS, since the FAIMS or the IMS does not destroy the analytes and these are still available at the output of the FAIMS or the IMS. With such an arrangement, a correlation between the measured data and the sensory evaluation of the released active substances can be established particularly well.

In a most preferred embodiment of the device according to the invention, the FAIMS is combined with a gas chromatograph (GC) and/or mass spectrometer (MS) and/or an olfactometer and/or an olfactory detection port (ODP) (sniffing port system) (52).

The activator 3 of the device according to the first aspect of the present invention, comprises an activator 31. The activator 31 is preferably in the form of a punch and is arranged at the lower end of the axis of the activator 3 and perpendicular to the plane of the support surface 8. The activator 31 is connected to a Z-positioning unit 32. The Z-positioning unit 32 enables the activator to be lowered and raised perpendicularly to the sample carrier 7 or to the support surface 8. By means of the Z-positioning unit 32, the activator 31 can be moved and positioned perpendicularly to the sample carrier 7 or to the support surface 8 and thus perpendicularly to the sample 6, i.e., to the active substance release system to be analyzed, preferably to the capsule or precursor 6 to be analyzed, on the sample carrier 7 or the support surface 8.

The Z-positioning unit 32 is either a positioning unit by means of which the activator 31 can be lowered manually or can be lowered above the sample to be analyzed by means of an electric drive/motor which is controlled via an EDP. Preferably, the positioning unit is an electric motor which controls the coordinates of the samples to be analyzed by means of an EDP control and lowers the activator 31 over the sample to be analyzed.

The activator 31 is configured to apply a physical and/or chemical pulse to the sample 6 to be analyzed, i.e., the release system 6, preferably the capsule 6 or the precursor 6, so that, in the case where the release system is a capsule, open the capsule, or in the case where the release system is a precursor, activate the precursor, and release the active ingredient contained therein.

The physical and/or chemical impulse is an action on the release system by pressure, friction, temperature, change of pH, UV radiation, ultrasound, microwave or a chemical reaction, by means of which the capsule is opened or the precursor is activated. For this purpose, the activator 31 is appropriately designed, for example as a friction head, UV lamp, pipetting module, etc.

If the release system is a capsule, it can be opened by various opening mechanisms, releasing the capsule contents or the active ingredient(s). In the majority of cases, the release system or capsule is opened by mechanical stress, for example by pressure or shear. Alternative opening mechanisms by which the active ingredient(s) can be released from the release system or capsule include temperature, change in pH, microwaves, light energy, for example UV radiation, or ultrasound.

Preferably, mechanical pressure and/or friction is applied perpendicularly to the sample 6 by means of the activator 31 in order to break open the release system, preferably the capsule, and release the active ingredient or ingredients contained therein. The mechanical pressure is generated by a pressure sensor 33. The pressure sensor 33 can be used to adjust the pressure applied to the active ingredient release system, preferably the capsule, in order to open it, i.e., cause it to burst or break.

In order to generate friction, which also leads to the breaking or besting of the active substance release system, the activation device comprises a rotation unit 38. The activator 31 is in direct connection with the rotation unit 38, which is driven by an electric motor. The rotation unit 38 sets the activator 31 in motion, for example by concentric, eccentric or isometric motion. In the concentric movement, the activator performs rotating circular movements on the sample 6 to be analyzed, the circles having different radii. In the eccentric movement, the activator performs rotating circular movements on the sample 6 to be analyzed, which lie outside the center of the circle. In the isometric movement, the activator moves back and forth like a carriage on the sample 6 to be analyzed in the X and Y directions.

By one of the above movements, the activator 31 moves over the sample 6 to be analyzed and creates a friction, releasing the active ingredient from the active ingredient release system, preferably the capsule.

In an alternative variant of the activation device 3, the rotation unit is an oscillator unit 38 which causes the activator 31 to oscillate. The oscillation of the activator above the sample 6 to be analyzed generates friction, which releases the active ingredient from the active ingredient release system, preferably the capsule.

Preferably, the activator 31 performs a concentric, eccentric or isometric movement on the sample 6 to be analyzed.

The surface of the activator 31 facing the sample 6 to be analyzed can be smooth or rough. In a preferred variant, the activator 31 has a rough surface. The rough surface increases the friction of the activator 31 on the release system, preferably the capsule. The surface material of the activator 31 is selected from the group consisting of Teflon, felt, sponge, terry cloth and other textiles, molleton, glass, metal and plexiglass. Preferred surface material of activator 31 is Teflon. Most preferred is felt because it produces high friction.

In an alternative embodiment, the activator 31 is configured to be used to generate other opening mechanisms to open the release system, preferably the capsule. For example, the activator 31 is configured to be used to generate temperature, UV radiation, magnetic radiation, ultrasound, or microwaves, which when acted upon will then open the release system, preferably the capsule, and release the capsule contents.

If the release system is a precursor or precursor substance, it can be activated by means of the activator 31 by triggering a chemical or physical impulse such as temperature, oxygen (oxidation), light, enzymes, microorganisms, chemical reaction (for example, hydrolysis), change in pH or moisture, etc., thereby releasing an active ingredient, preferably an odiferous substance.

In a preferred embodiment, the active ingredient or ingredients released is/are volatile substances.

The activation device 3 further comprises a detection line 35. The released active ingredient or the multiple released active ingredients, which are preferably present as a gas phase, are captured by means of a detection line 35 and fed to the detection device 5. In a preferred variant, the activation device is set up in such a way that, by means of an integrated suction mechanism, the active ingredient or active ingredients released from the release system are sucked in and fed to the detection device 5.

In an alternative and preferred embodiment, the activation device 3 further comprises a collection container 34 at its lower end, which can enclose the sample 6 to be analyzed and the activator 31 when the collection container is placed on the sample support 7 or the support surface 8. The collection container 34 has a detection line 35 for collecting a released activator and a purge line 36.

In order to prevent a released active ingredient, in particular a gaseous or volatile active ingredient, for example an odiferous substance or a flavoring, from escaping from the area of the surface of the sample carrier 7 or the support surface 8 covered by the collecting container 34 without reaching the detection device or the analysis device 5, the collecting container 34 is preferably designed in such a way that it is closed laterally and at its upper end and open at its lower end and the end facing the sample to be analyzed. When the activation device 3 is lowered over the sample to be analyzed and rests on the sample carrier 7 or the support surface 8, the collecting container closes gas-tight with the covered surface.

In a preferred embodiment, the collection container 34 has a bell shape.

In order to further prevent a released active substance from escaping from the area of the surface of the sample carrier 7 or the supporting surface 8 covered by the collecting container or the bell 34 without reaching the detection device or the analysis device 5, the collecting container or the bell 34 can be provided with a round edge which can be flush with the underlying supporting surface or with a sealing arrangement which allows a tight fit of the bell to the covered area, so that the active substance which is released and is to be analyzed can escape exclusively via the detection line 35 and can thus be inevitably fed to the detection device, respective the analysis device. For example, the collection container may include a sealing ring which may be formed of a fluoroelastomer.

The collection container or bell 34 may be made of a transparent material, such as glass or plastic. The transparency of the collection container or bell 34 has the advantage that during the execution of the opening or activation of the release system, preferably the capsule 6 or the precursor 6, the release of the active ingredient or the multiple active ingredients and the analysis, the surface covered with the collection container or bell 34 can be viewed.

The collection container or bell 34 is arranged on the activation device 3 in such a way that it can be lowered or moved upwards together with the activator 31 by means of the Z-positioning unit 32 perpendicular to the sample carrier 8 or the support surface 8.

A transparent collection container 34 also has the advantageous effect that, alternatively, an opening or activation of the release system, preferably of the capsule 6 or of the precursor 6, and release of one or more active ingredients by means of light or by UV radiation, instead of the activator, can take place by direct irradiation through the collection container 34 onto the sample to be analyzed.

In a further embodiment of the device according to the invention, the collecting container or the bell 34 can be lowered or moved upwards perpendicular to the sample carrier 8 or to the support surface 8 independently of the Z-positioning of the activator 31.

In an alternative and preferred embodiment, the activation device 3 comprises a detection line 35 which is connected to the collection container or bell 34. The detection line 35 is configured to deliver the active agent or agents released from the release system to the detection device 5. The detection line is preferably made of metal or a plastic polymer.

Preferably, the active substance released and to be analyzed is a volatile substance, for example a volatile odorant or flavoring, or a mixture of volatile odorants or flavorings, which is/are fed directly to the detection device 5 for analysis. In a preferred embodiment, the volatile substance (s) is/are delivered to the detection device 5 via an integrated aspiration mechanism aspirated by the detection power 35. Otherwise, and in an alternative variant, the released active substance reaches the detection device or analysis device 5 by means of expulsion through an inert gas, e.g., nitrogen or helium. For this purpose, inert gas is introduced into the collection container via a line connected to the collection container or bell 34, whereby the volatile substance or substances is/are expelled and passed to the detection device 5.

Optionally, the activation device 3 comprises a purge line 36 which is connected to the collection container or bell 34. The purge line 36 is adapted to supply a purge gas or purge liquid to the system after completion of the opening, release, and analysis process to purge the collection container or bell 34 and or detection line 35. The purging removes traces of agents so that the system is free of contamination for the next analysis procedure. The purge gas is preferably selected from air, nitrogen or helium. The purge liquid is preferably water or polar or non-polar solvents, preferably ethanol, acetone, isopropanol, heptane, or aqueous detergent solutions, the latter if necessary, in combination with a final further rinsing step. Otherwise, wait between two analysis steps until the residues of volatile active substances have evaporated.

A fan 39, which is optionally a component of the activation device 3, can be used to blow off residual rinsing gas or rinsing liquid, residual active ingredients of the encapsulated active ingredient and other sample residues from the activation device 3, preferably from the collection container 34 and/or from the activator 31.

The device according to the first aspect of the present invention further comprises a computer system 51 with suitable software, for controlling and positioning the device 1 and for evaluating and storing the measurement results.

In a preferred variant, the X/Y positioning units (4) of the device according to the first aspect of the invention comprise a positioning laser (43). The positioning laser (43) is part of the positioning unit of the computer system or computer 51 through which the movement of the X-axis 21, the Y-axis 22 and the activation device 3 is controlled.

The sample carrier 7 preferably has a grid of evenly spaced horizontal and vertical lines which create a grid of uniform sample fields. A sample field forms the surface on which the sample to be analyzed is applied or positioned.

For the positioning and movement of the activation device 3 above the sample carrier 7, the start and end measuring points of the sample fields and the number of horizontal and vertical sample fields on the sample carrier 7 are required for the adjustment (teaching) of the device 1. These positions are determined by a position laser 43 and stored in the fixture 1 via the computer system. Based on the determined and stored start and end measuring points of the sample fields, which were defined by means of the position laser, the activation device 3 can be positioned exactly over the sample field to be analyzed and a sample field can be traversed.

To start a measurement or a series of measurements, or before the start of the breakup, release and analysis process, the X-axis 21, the Y-axis 22 and the activation device 3 are each moved to the "zero points", i.e., the starting points, of the base frame 2. As soon as the "zero" points are reached, a signal is sent to the computer. Based on these "zero" points, in combination with the movement of the positioning units, the start and end points can each be assigned to a coordinate. Using these coordinates in conjunction with the number of measurements in the horizontal and vertical, a coordinate can be calculated for each measuring point and approached accordingly in an automated manner.

With the device 1 for the analytical and/or sensory determination of a release system and/or an encapsulated active substance according to the first aspect of the present invention, a system is provided which enables an objective and standardized analytical method to be carried out. This in turn enables objective qualitative and/or quantitative statements to be made about the release of an active ingredient or several active ingredients, for example the concentration of the released active ingredient, the release rate or the release profile and/or statements to be made about the properties of an active ingredient release system, preferably a capsule or a precursor, for example the mechanical stability, breaking strength or the retardation behavior of a capsule after storage over a certain period of time.

Furthermore, in accordance with the first aspect of the present invention, the device 1 operates fully automatically. The fully automatic device 1 has the advantage of allowing, for example, the precise setting of the following analytical parameters: pressure, time lengths of the pressure-free measurement, abandonment of pressure without friction, friction process and the friction-free detection time, rotation speed, rotation duration or purging time. By means of the device 1 according to the invention, an analytical and/or sensory determination can be carried out simultaneously, allowing correlation of the measurement results obtained. Furthermore, the device 1 according to the invention enables a real-time analysis of the release of one or more active substances from a release system used according to the invention.

Furthermore, the device 1 according to the invention enables for the first time a reproducible, objective analytical and/or sensory determination of the burst behavior of encapsulated active ingredients, for example odiferous substances or flavorings. This enables the screening of new capsule technologies and capsule further developments for capsules with the best burst behavior, without great expenditure of time and personnel and without negative influences of the subjectivity of a sensory panel.

In a second aspect, the present invention is therefore directed to a method for analytically and/or sensory determination of the release of one or more active ingredients from a release system, preferably from a capsule or precursor.

A release system 6 in the context of the present invention is understood to mean a solid preparation, for example particles or a capsule 6, containing one or more active ingredient(s), or a precursor 6 or a precursor substance, as defined above.

The capsules 6 analyzed by the method of the invention are preferably those selected from the group consisting of hard-shelled capsules, soft-shelled capsules, macrocapsules, microcapsules, capsule lurries and capsule emulsions.

The active ingredient contained in the release system, preferably the active ingredient contained in the capsule or the active ingredient released from the precursor, are solid, liquid or gaseous substances.

Preferably, the active ingredient of the release system is a volatile substance which is volatile at room temperature, and which is preferably selected from the group consisting of odiferous substances, flavorings, perfume oils, odiferous substance mixtures, flavoring mixtures, aromatic substances, plant extracts, essential oils, cosmetic active ingredients, cooling active ingredients and pharmaceutical active ingredients. As far as the individual active ingredients are concerned, reference is made to the above description.

In a first step of the method according to the invention, a sample 6, namely a release system 6 to be analyzed comprising one or more active ingredients, is provided on a sample carrier 7 located on a support surface 8.

For example, in order to test the distribution or adhesion of an active ingredient release system on a particular substrate, the sample carrier 7 can also be a fabric, for example clothing, linen, etc. made of cotton, linen, wool, viscose, polyacrylic, polyamide, polyester, or another organic or inorganic substrate or its surface, for example tiles, linoleum, wood, glass, metal, hair, etc., or can be a fiber blanket.

Alternatively, the release system 6, preferably a capsule 6 or a precursor 6, is located directly on the support surface 8 in the process according to the invention.

In the alternative variant, where the sample 6 is located directly on the support surface 8, for example in the case of a floor cleaning agent with an encapsulated active ingredient 6 or a precursor 6, the device according to the invention is positioned directly above the support surface and the analysis will be carried out directly on the surface of the support surface 8.

The applied amount of the release system 6, preferably of the capsule 6 or of the precursor 6, on the sample carrier 7 is variable and is dimensioned depending on the material and diameter of the rubbing head, the application of the capsule or of the precursor as well as the active substance content in the capsule or of the precursor. The application to the sample carrier is preferably in the form of a capsule slurry, preferably in a concentration close to the application, for example, taking into account the concentration in a standard washing suds in a washing machine as well as taking into account the average adhesion of the capsules to the laundry in a washing process. The applied amount is 0.1 mg to 2.0 mg capsule or precursor per measurement field or sample field, even more preferably 0.3 to 1.8 mg and most preferably 0.5 to 1.0 mg capsule or precursor per measurement field or sample field on the sample carrier.

Alternatively, for example, when determining the adhesion of a release system to a fabric after a machine wash, the amount of release system is adjusted to the application.

The sample carrier 7 preferably has a grid of evenly spaced horizontal and vertical lines, creating a grid of evenly spaced measurement or sample fields. The sample 6 to be analyzed, i.e., the release system 6 to be analyzed, preferably the capsule 6 or the precursor 6, is applied to the sample carrier 7 within a specific measurement or sample field which has individual coordinates. By teaching the device according to the invention (via the laser) and specifying rows and columns before starting a measurement, the grid coordinates are independently calculated and controlled by the EDP. This allows the activation device 3 to be controlled to the corresponding sample field on which the sample to be analyzed is applied or positioned.

In a next step of the method according to the invention, the activation device 3 with an activator 31 is positioned above the release system 6, in particular the capsule 6 or the precursor 6. The movement and positioning of the activation device 3 with the activator 31 are carried out via the X-axis 21 and the Y-axis 22 or via the X-positioning unit/drive 41 and the Y-positioning unit/drive horizontally and in the X- and Y-directions relative to the sample carrier 7 or the support surface 8 on which the sample to be analyzed lies.

In a further step of the method according to the second aspect of the invention, the activation device 3 is lowered so that the activator 31 maintains a distance from the release system 6, in particular from the capsule or precursor, or slightly contacts the release system 6. This is done depending on the impulse used to open or activate the release system. In the case of opening or activation by means of pressure and/or friction, the activator 31 touches the release system, whereas in the case of opening or activation by means of UV radiation, a distance to the release system can be maintained.

Next, in the process according to the invention, the active ingredient or the plurality of active ingredients is/are released from the release system 6, preferably from the capsule 6 or the precursor 6, by means of the activator. The release of the active ingredient or the plurality of active ingredients is effected by a physical and/or a chemical impulse. If the release system is a capsule, the release of the active ingredient occurs by opening the capsule by means of pressure, friction, temperature, change in pH, UV radiation, microwaves and ultrasound. If the release system 6 is a precursor 6, the release of the active ingredient from the precursor substance occurs by chemical reaction, temperature, humidity, change of pH, oxygen (oxidation), light, for example UV radiation, enzymes and microorganisms.

In a preferred variant of the method, the release of the active ingredient or the plurality of active ingredients from a capsule by means of the activator is effected by pressure on the sample 6 to be analyzed and/or friction of the sample 6 to be analyzed. Depending on the capsule material, for example in the case of a thin capsule wall or in the case of an unstable capsule material, in an alternative variant of the method according to the invention the capsule is broken only by applying pressure and without friction.

The mechanical pressure is generated via a pressure sensor 33. The pressure sensor 33 can be used to set the pressure that is applied to the active substance release system, preferably the capsule, in order to cause it to burst or break. The pressure in the process according to the invention that is applied to the active substance release system, preferably the capsule, in order to break it and release the active substance is ≥0 Pa. Already a pressure of 0 Pa, i.e., when simply approaching the activator 31 to the sample 6 to be analyzed, is demonstrably already sufficient to break first capsules. Preferably, the procedure is carried out at a pressure in the range of 1000 Pa to 30000 Pa, even more preferably at a pressure in the range of 2500 Pa to 25000 Pa, on the active substance release system, preferably the capsule, or the sample carrier 7. These values preferably refer to a radius of 2 cm. By changing the radii of the activator or the selection of the rubbing head material, the above minimum and maximum pressures are adjusted.

In order to generate friction, which also leads to the breaking or besting of the active substance release system, the activation device comprises a rotation unit 38. The activator 31 is in direct connection with the rotation unit 38, which is driven by an electric motor. The rotation unit 38 sets the activator 31 in motion, for example by concentric, eccentric or isometric motion. In the concentric movement, the activator performs rotating circular movements on the sample 6 to be analyzed, the circles having different radii. In the eccentric movement, the activator performs rotating circular movements on the sample 6 to be analyzed, which are outside the center of the circle. In the isometric movement, the activator moves back and forth like a carriage on the sample 6 to be analyzed in the X and Y directions.

One of these movements causes the activator 31 to travel over the sample 6 to be analyzed and create friction, releasing the active ingredient from the release system, preferably the capsule.

In an alternative embodiment, activator 31 is an oscillator unit 38 that causes the activator 31 to oscillate. Oscillation of the activator over the sample 6 to be analyzed generates friction, which releases the active ingredient from the release system, preferably the capsule.

In another alternative embodiment, the direction of rotation of the activator can be changed at short intervals during the measurement, causing the active ingredient to be released from the active ingredient release system, preferably the capsule.

The release of the active ingredient from the release system 6, in particular from the capsule 6, by means of the activator 31 in the process according to the invention is carried out at a rotational speed of the activator 31 on contact with the encapsulated active ingredient 6 and/or the sample carrier 7 from 0 rpm, preferably at a rotational speed of 50 rpm to 1,000 rpm and even more preferably at a rotational speed of 200 rpm to 1,000 rpm.

The friction time in the process according to the invention is variable. It is preferably 0 to 30 s.

The process parameters pressure and friction have the greatest influence on the breaking of the capsule. Advantageously, these two process parameters can be precisely set with the automated process according to the invention. Due to the adjustment of different process parameters, it is also possible to break capsules of different sizes and capsule walls of different thickness. Furthermore, an increase in pressure, for example, enables a faster release of the active ingredient or active ingredients from the release system, whereby stronger intensities can be measured in the subsequent analytical and/or sensory determination Conversely, the applied pressure for bursting the capsule can be seen as a parameter for the breaking strength and thus the stability of a capsule.

In a preferred embodiment, the active ingredient or the multiple ingredients released are a volatile substance.

In a further step of the process according to the invention, the released active ingredient(s), which are preferably present in the gas phase, are captured by means of a detection line 35 and fed to the detection device 5. In a preferred variant, in the process according to the invention, by means of an integrated suction mechanism, preferably the pump of a FAIMS, the active ingredient(s) released from the release system is/are sucked in and fed to the detection device 5.

In a preferred variant of the method according to the invention, in order to prevent a released active ingredient, in particular a gaseous or volatile active ingredient, for example an odiferous substance or a flavoring, from escaping during the analytical and/or sensory determination, the surface of the sample carrier 7 or the support surface 8 on which the sample is located is covered with a collecting container 34, which preferably has a bell shape and which is arranged at the lower end of the activator 31. For this purpose, the collecting container 34 is preferably designed in such a way that it is closed laterally and at its upper end and open at its lower end and the end facing the sample to be analyzed. When the activation device 3 is lowered above the sample to be analyzed and rests on the sample carrier 7 or the support surface 8, the collecting container closes gas-tight with the covered surface. This prevents a released active ingredient, in particular a volatile active ingredient, for example an odiferous substance or a flavoring, from escaping from the area of the surface of the sample carrier 7 or the support surface 8 covered with the collection container 34 without reaching the detection device or the analysis device 5.

In an optional variant, the released active ingredient can be sucked out of the collection container or the bell jar to the detection device or the analysis device 5 by means of a pump. This has the advantage that the released active substance can be detected after only a few seconds.

The active ingredient released from the release system, preferably the capsule or the precursor, is fed in a further step of the process according to the invention to a detection device or an analysis device 5 for analytical and/or sensory determination of the released active ingredient.

By means of the detection device or analysis device 5, the analytical and/or sensory determination of the active substance released from the release system is carried out in a further step of the method according to the invention.

Analytical investigation and/or determination is understood to mean a sensory, qualitative (identification of the active ingredient) and/or quantitative (quantity of the active ingredient) analysis of an active ingredient released from the release system 6, in particular from a capsule 6 or a precursor 6. Advantageously, the method according to the invention can be used to analyze the active ingredient or the active ingredients of a release system, for example the encapsulated active ingredient or the encapsulated active ingredients, according to type and quantity.

The detection device or analysis device 5 is such measuring equipment that enables a qualitative and/or quantitative analysis of the released active substance.

For qualitative and/or quantitative analysis of the released active ingredient(s), detection devices or analysis devices 5 are preferably used, which are preferably selected from the group consisting of gas chromatograph (GC), gas chromatograph/mass spectrometer (GC/MS), ion mobility spectrometry (IMS), FAIMS (high field asymmetric waveform ion mobility spectrometry), GC-FAIMS and GC-MS-FAIMS or combinations of the aforementioned measuring devices.

Preferably, the detection device or analysis device 5, IMS (ion mobility spectrometry), FAIMS (high field asymmetric waveform ion mobility spectrometry), GC-FAIMS and GC-MS-FAIMS or a combination of the aforementioned measuring devices is used for analysis.

Most preferably, in the method according to the invention, the analytical determination of the released active ingredient is carried out by means of FAIMS (high field asymmetric waveform ion mobility spectrometry). FAIMS allows detection and analysis of volatile chemical species directly from a gas stream or from the gas phase over a liquid or solid sample. There are two mechanisms for delivering the sample to the FAIMS unit: single sampling or continuous sampling. In single sampling, a defined volume of the gaseous analyte, i.e., the released active ingredient(s) is/are collected or adsorptively enriched in an upstream step and fed to the FAIMS. In continuous sampling, the gaseous analyte, i.e., the released active ingredient, is continuously fed to the FAIMS by means of a carrier gas, for example purified air or argon. Preferably, the sampling is performed continuously, which allows the analytical determination of the released active ingredient(s) to be performed in real time. This enables an analytical determination of the real-time release, which is particularly advantageous when determining the release of odiferous substance or flavoring mixtures.

In an alternative variant of the method according to the invention, the released active ingredient(s) is/are bound to an adsorbent, for example in a Tenax tube, in order to concentrate them and then measured by GC-MS (dynamic headspace method). In the dynamic headspace technique, the active ingredient(s) released during the measurement is/are directed to a suitable adsorbent material, for example in a Tenax tube, or to a cold trap via a continuous air flow, which is generated by the FAIMS, for example, or for which an additional external pump is used, or an inert gas. For this purpose, the adsorbent-containing glass tube can either be directly incorporated into the air flow from the CBA, or the active ingredient(s) is/are first (if the air flow is too high for the direct method) passed into a closed container (e.g., a plastic bag), and then the active ingredient(s) is/are passed onto the adsorbent with a lower air flow. The Tenax tube (adsorbent) or trap is then heated and the enriched analytes pass to the FAIMS, for example, or onto the column for gas chromatographic analysis.

In a preferred variant of the method according to the invention, in addition to the qualitative and quantitative determination of the released active ingredient, a sensory determination of the released active ingredient is carried out simultaneously by means of an olfactometer and/or an olfactory detection port (ODP) (sniffing port system) (52), which is connected via an alternative output to the detection device or analysis device 5. Such a combination allows to establish a correlation between the analytical and sensory determination.

In the device according to the invention, the sniffing port system can be arranged both in front of the detection device 5 and behind the detection device 5. The arrangement of the sniffing port system behind the detection device 5 is particularly advantageous if the detection device 5 is a FAIMS or an IMS, since the FAIMS or the IMS does not destroy the analytes and these are still available at the output of the FAIMS or the IMS. With such an arrangement, a correlation between the measured data and the sensory evaluation of the released active substances can be established particularly well.

The measurement results obtained are fed to an EDP system 51 with suitable software and evaluated and stored by means of the software.

In a final step of the method according to the invention, resetting of the device 1 is performed, wherein resetting of the device 1 comprises the following steps: First, the activation device 3 is raised by means of the Z-positioning unit 32.

Optionally, the method according to the invention comprises a step in which the activator 31 and/or the detection line 35 and/or the detection device are flushed with a purge gas or a purge liquid after completion of the opening, release and analysis process. The purging removes residues of released active ingredients or other sample residues so that the system is free of contamination for the next analysis procedure. The purge gas is preferably selected from air, nitrogen or helium. The purge liquid is preferably water or polar or non-polar solvents, preferably ethanol, acetone, isopropanol, heptane, or aqueous detergent solutions, the latter if necessary, in combination with a final further rinsing step. Otherwise, wait between two analysis steps until the residues of released active substances have evaporated.

A fan 39, which is optionally a component of the activation device 3, can be used in the process according to the invention to blow off residual purge gas or purge liquid, residual active ingredients of the encapsulated active ingredient and other sample residues from the activation device 3, preferably from the activator 31 and/or from the collecting vessel 34.

Figure 5:
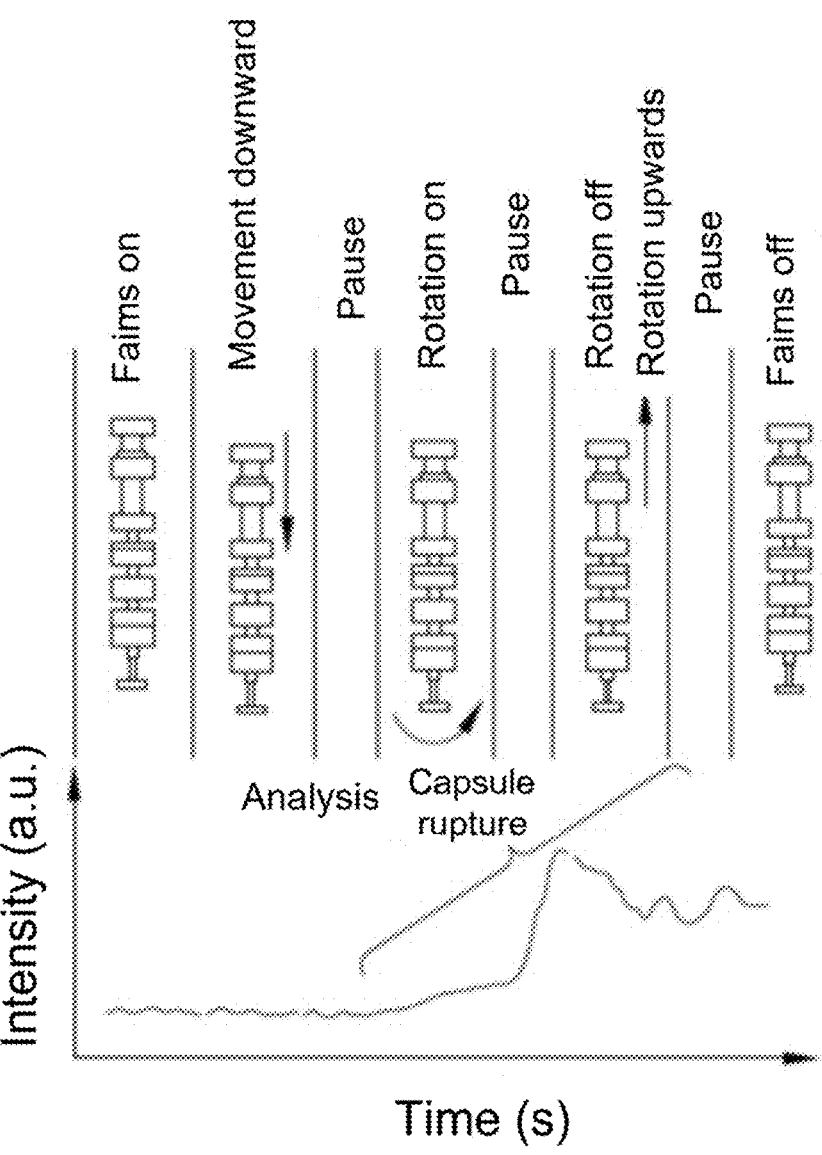
FIG. 5 is a schematic representation of the steps of the analysis procedure according to the present invention.

A schematic overview of the steps of the process according to the invention is shown in FIG. 5.

With the method according to the second aspect of the present invention, it is possible to analyze active ingredients from release systems, preferably capsules or precursors, objectively and under standardized conditions, i.e., setting defined process parameters. With the analytical method according to the invention, active ingredient release systems, preferably capsules or precursors, can be broken open under clearly defined conditions (for example pressure), i.e., in a standardized and controlled manner, and the capsule contents can be analyzed quantitatively and/or qualitatively at the same time. This enables a standardized and reproducible analytical procedure, which is unified by norms, in which the conditions of its applicability and its procedure are defined in such a way that the same results can be expected under the same conditions. This also makes it possible to compare measurement results from different capsule samples or precursors. Such an analytical and/or sensory determination under reproducible conditions of release is not yet known.

In turn, the reproducible, objective analytical and/or sensory determination of the burst behavior of encapsulated active ingredients according to the method of the invention enables the screening of new capsule technologies and capsule further developments for capsules with the best burst behavior, without great expenditure of time and personnel and without negative influences of the subjectivity of a sensory panel.

The method according to the invention also enables, for the first time, continuous on-line measurement of the release of one or more active ingredients from a capsule or from a precursor, whereby the time sequence of the release can be recorded directly, i.e., in parallel with the release. An example of such an on-line measurement is shown in FIG. 6.

Figure 6:
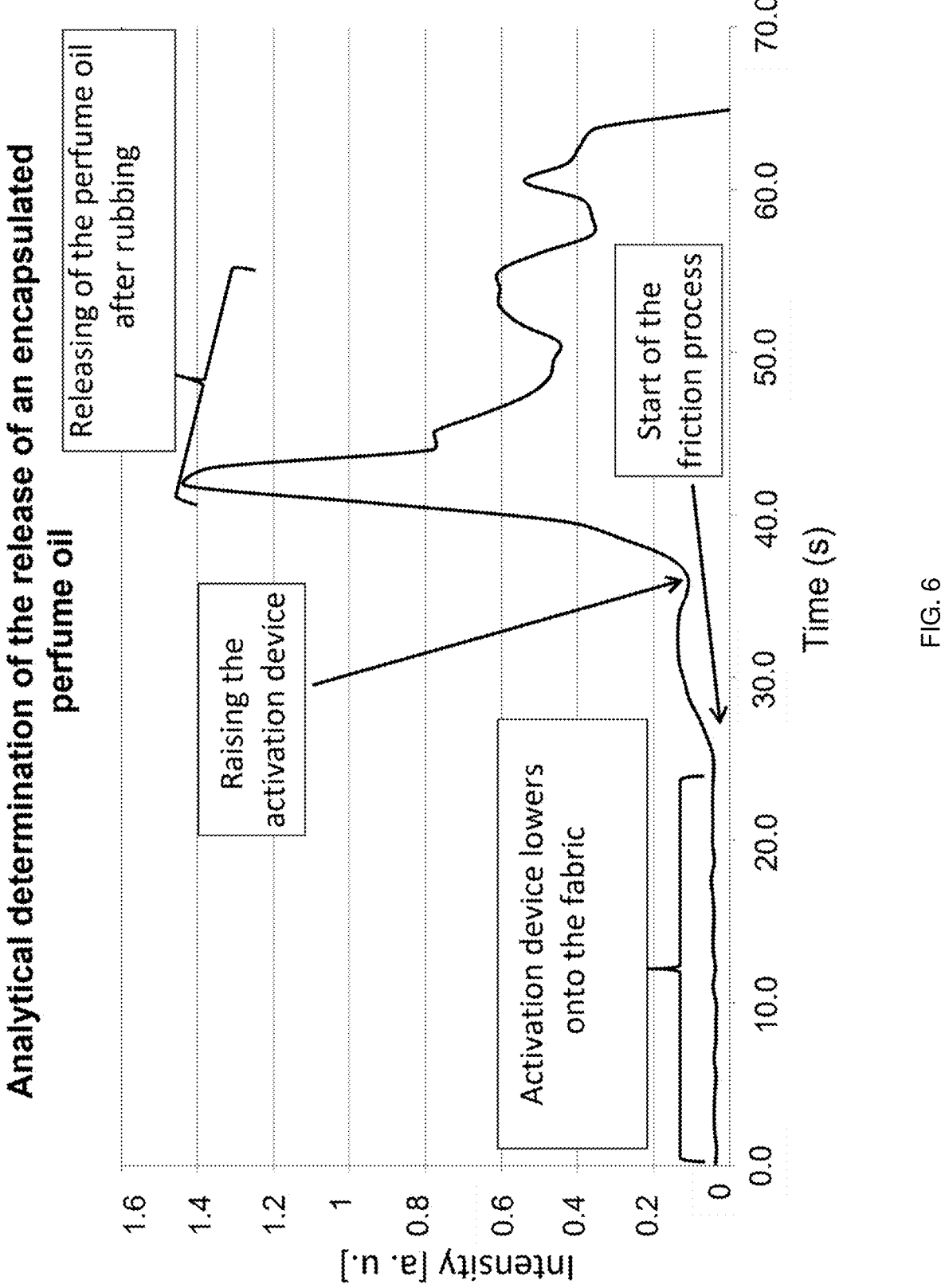
FIG. 6 shows an example of a continuous measurement of the capsule burst of a capsule containing perfume oil.

FIG. 6 shows the course of a continuous measurement of the capsule burst of a capsule containing perfume oil. The capsule is a multilayer capsule with a liquid perfume oil core. Measurement parameters: 10 s rubbing at 60 rpm at 1.0 N; 30 s post-rub time.

The capsule burst (capsule rupture) and the release of the perfume oil are particularly visible after lifting the grating head. The maximum of the release curve is reproducible and can be used to compare different capsules.

The method according to the invention also enables continuous operation in which several samples can be analyzed in succession, for example under the same process parameters. Thus, the analysis values can be directly compared with each other. In addition, via a combination of detection device 5 with an alternative output for an olfactometer and/or an olfactory detection port (ODP) (sniffing port system) 52, improved sensory evaluations and comparisons of different samples can take place due to the reproducible release method. In addition, the analytical and sensory measurement results obtained in this way can be correlated with each other.

Based on the advantages described above, the device and method according to the invention are preferably suitable for the analytical and/or sensory determination of the release of an active ingredient from a release system 6, preferably from a capsule 6 or a precursor 6, to analyze the composition of the active ingredient according to type and amount.

The method according to the invention can also be used to analyze the mechanical stability and crushing behavior of different capsule materials, especially in the development and production of new capsules. In addition, the method according to the invention allows the determination of the retardation behavior of capsules to be analyzed, preferably after storage of the capsules for a certain period of time.

The method according to the invention also enables a comparison of the release behavior of different active ingredients, for example of different odorants or flavorings or odorant or aroma mixtures, from a release system, preferably from a capsule or a precursor.

The method according to the invention also allows the analysis of the distribution and adhesion of microcapsules on surfaces, for example the distribution and adhesion of microcapsules containing an odiferous substance, after washing and drying textiles.

The method according to the invention further enables the analysis of the substantivity of one or more active ingredients after release from the release system 6, in particular from a capsule 6 or a precursor 6, on a substrate;

In addition, the method according to the invention can be used to analyze the influence of physical or chemical factors, for example temperature, light, UV radiation, pH, on the mechanical stability and fracture strength of a release system, in particular a capsule or a precursor 6 and/or on the release of an active substance or of several active substances from a release system 6, in particular from a capsule 6 or a precursor 6.

In addition, the method according to the invention can be used during the development and production of the release system 6 for the analytical determination of the release of an active ingredient or several active ingredients and for the determination of the properties of a release system 6, in particular a capsule 6 or a precursor 6.

In a final aspect, therefore, the present invention relates to the use of the device and method according to the present invention for the analytical and/or sensory determination of the release of an active substance or several active substances, in particular of the concentration, the release rate or the release profile from a release system (6), in particular from a capsule (6) or a precursor (6);

for determining the properties, in particular the mechanical stability, the breaking strength and the retardation behavior, of a release system (6), in particular of a capsule (6) or a precursor (6), in particular the mechanical stability, the breaking strength or the retardation behavior, of capsules (6) made from different capsule materials and different active ingredients;

for analyzing the distribution and adhesion of a release system (6), in particular a capsule (6) or a precursor (6), on a substrate, in particular after washing and drying textiles;

for analyzing the substantivity of an active substance or several active substances after release from the release system 6, in particular from a capsule 6 or a precursor 6, on a substrate;

for analyzing the influence of physical or chemical factors, for example temperature, light, UV radiation, pH, on the mechanical stability and breaking strength of a release system, in particular of a capsule or a precursor 6 and/or on the release of an active ingredient or of several active ingredients from a release system 6, in particular from a capsule 6 or a precursor 6; and for the analytical determination of the release of an active substance or several active substances and for the determination of the properties of a release system 6, in particular of a capsule 6 or a precursor 6, during the development and production of a release system 6.

EXAMPLE 1

Comparison of Fragrance Release from Different Capsule Technologies

Comparison of the analytical burst behavior of different capsule types. Type A to type D are methylformamide-based core/shell perfume oil capsules and differ in their wall thickness (decreasing wall thickness from A to D). All capsule types were loaded with the same perfume oil at the same dosage. The measurement was performed at 2.5 N for 15 s; friction: 100 rpm.

Figure 7:
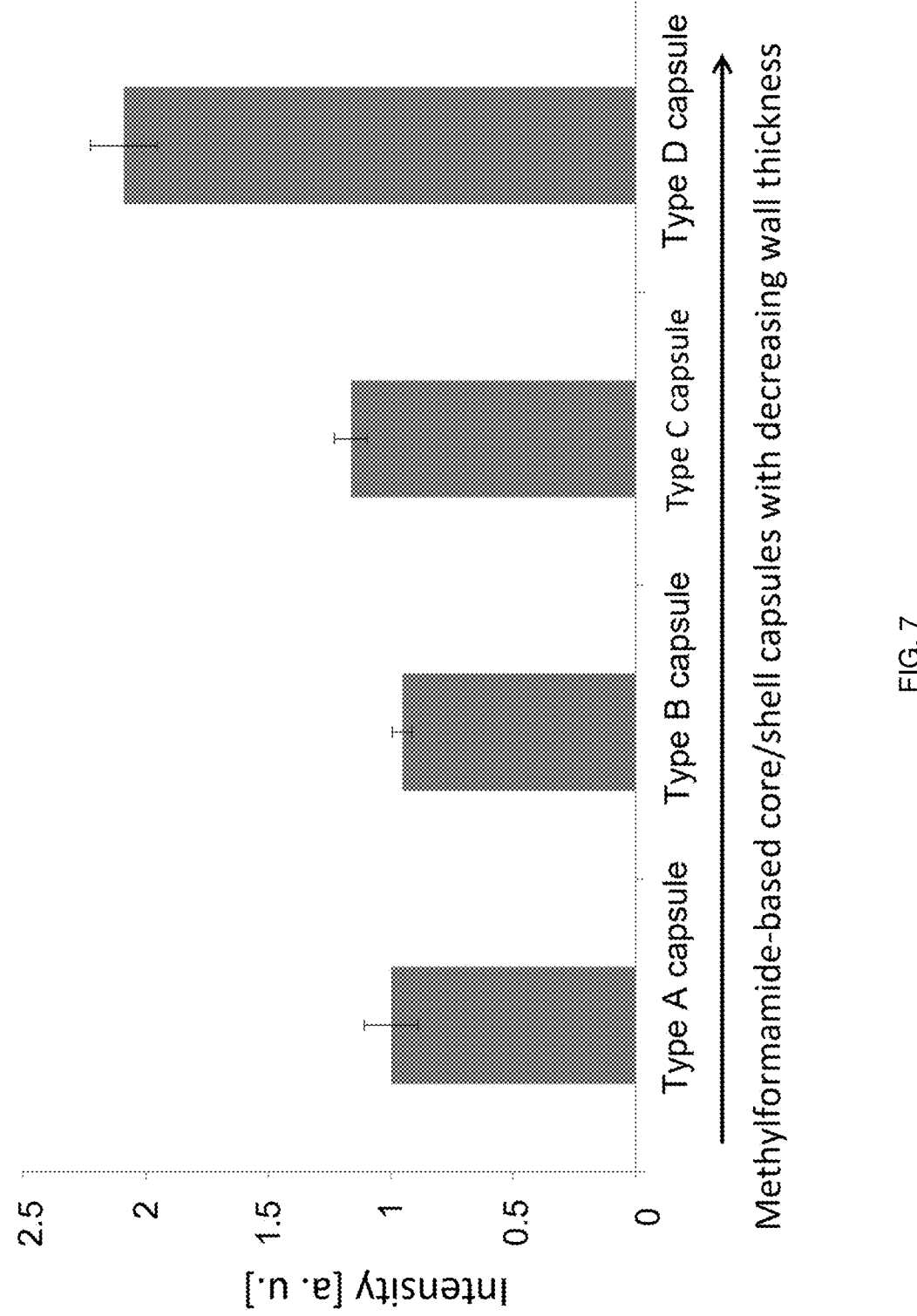
FIG. 7 shows a comparison of the fragrance release from methylformamide-based core/shell perfume oil capsules with different wall thicknesses

The results of the maximum burst intensity are shown in FIG. 7. The burst intensity is highest for the type D capsule with the smallest wall thickness.

LIST OF REFERENCE SIGNS

1 Device
2 Base frame
21 X axis
22 Y axis
3 Activation device
31 Activator
32 Z positioning unit
33 Pressure sensor
34 Collection container/bell
35 Detection line
36 Purge line
37 Purge pump
38 Rotation unit
39 Fan
4 X/Y positioning units
41 X positioning unit/X positioning drive
42 Y positioning unit/Y positioning drive
43 Positioning laser
5 Detection device/analysis device
51 EDP system
52 Sniffing port system
6 Sample/release system/capsule/precursor
7 Sample carrier
8 Support surface

The invention claimed is:

1. A device suitable for the analytical and/or sensory determination of the release of one or more active substances from a release system, and/or for determining the properties of a release system, comprising:

(a) a base frame;

(b) a sample carrier or a supporting surface connected to the base frame and on which the release system is to be located, the release system being a capsule or a precursor:

(c) an activation device which is connected to the base frame and which is adapted to open or activate the release system and to release the one or more active substances;

wherein the activation device comprises:

an activator for exerting a physical or chemical impulse on the release system in order to release the one or more active substances, a collection container for enclosing the release system on the sample carrier or supporting surface and the activator when the collection container is placed on the sample carrier or the supporting surface, and a Z-positioning unit connected to the activator and the collection container to move the activator and the collection container perpendicularly to the sample carrier or the supporting surface; and and (d) a detection device in communication with the activation device to receive the one or more released active substances from the activation device for the analytical determination of the one or more released active substances.

2. The device according to claim 1, wherein the activation device further comprises:

a detection line for collecting the one or more released active substances and guiding them to the detection device.

3. The device of claim 2, further comprising a purge line connected to the detection line and arranged to supply a purge gas or a purge liquid to the detection line.

4. The device according to claim 1, wherein the physical or chemical pulse exerted on the capsule by the activation device is selected from one or more in the group of pressure, friction, temperature, change in pH, UV radiation, microwaves and ultrasound, or wherein the physical or chemical pulse exerted on the precursor by the activation device is selected from one or more in the group of chemical reaction, temperature, humidity, change in pH, oxygen (oxidation), light, enzymes and microorganisms.

5. The device according to claim 1, wherein the activator has a rough surface.

6. The device according to claim 1, wherein the activation device comprises a rotation unit which triggers concentric, eccentric or isometric movement at the activator.

7. The device according to claim 1, further comprising:

at least one X positioning unit and/or Y positioning unit, which is connected to the base frame and which is arranged to move the activation device relative to the sample carrier or the supporting surface.

8. The device according to claim 7, wherein the at least one X positioning unit and/or Y positioning unit comprises a positioning laser.

9. The device of claim 1, wherein the release system comprises a capsule.

10. Method for the analytical and/or sensory determination of the release of one or more active substances from a release system wherein the release system is a capsule or a precursor, the method comprising the following steps:

(i) providing the release system comprising one or more active substances, on a sample carrier or on a support surface;

(ii) positioning an activation device with an activator and a collection container over the release system;

(iii) lowering the activation device, so that the collection container encloses the release system and the activator when the collection container is supported on the sample carrier or the support surface;

(iv) releasing the one or more active substances from the release system by means of the activator;

(v) collecting and delivering the released one or more active substances to a detection device; and (vi) determining, analytically and/or sensorily, the one or more released active substances from the release system; and/or determining the properties of the release system; and/or analyzing the distribution and adhesion of the release system on a substrate; and/or analyzing the substantivity of one or more active substances after release from the release system on a substrate; and/or analyzing the influence of physical or chemical factors on the mechanical stability and breaking strength of the release system and/or on the release of one or more active substances from the release system; and/or determining analytically the release of one or more active substances for determining the properties of the release system during the development and production of the release system.

11. The method according to claim 10, further comprising, after step (vi):

(vii) resetting the device, wherein resetting the device comprises one or more of the following steps:

($\alpha$) raising the activation device;

($\beta$) purging the activator and/or a detection line and/or the detection device with a purge gas or a purge liquid; and ($\gamma$) blowing off residues of the one or more released active substances and/or other sample residues from the activation device.

12. The method according to claim 10, wherein the release of the one or more active substances by means of the activator is followed by a physical pulse or a chemical pulse on the capsule or on the precursor.

13. The method according to claim 12, wherein the physical or chemical pulse on the capsule is selected from one or more in the group of pressure, friction, temperature, change in pH, UV radiation, microwaves, and ultrasound, or the physical or chemical pulse on the precursor is selected from one or more in the group of chemical reaction, temperature, humidity, change in pH, oxygen (oxidation), light, enzymes, and microorganisms.

14. The method according to claim 10, wherein the release of the one or more active substances by means of the activator is carried out at a pressure of in a range of 1000 Pa to 30000 Pa.

15. The method according to claim 10, wherein the release of the one or more active substances by means of the activator is carried out at a rotational speed of the activator on contact with the release system and/or the sample in a range of 50 rpm to 1,000 rpm.

16. The method according to claim 10, wherein the release system is selected from one or more in the group of: hard-shelled capsules, soft-shelled capsules, macrocapsules, microcapsules, capsule slurries and capsule emulsions.

17. The method according to claim 10, wherein the one or more active substances is selected from one or more in the group of odiferous substances, flavorings, perfume oils, odiferous substance mixtures, flavoring mixtures, aromas, plant extracts, essential oils, cosmetic active substances, cooling active substances, pharmaceutical active substances.

* * * * *